US007222026B2

(12) United States Patent
Matsushita et al.

(10) Patent No.: US 7,222,026 B2
(45) Date of Patent: May 22, 2007

(54) EQUIPMENT FOR AND METHOD OF DETECTING FAULTS IN SEMICONDUCTOR INTEGRATED CIRCUITS

(75) Inventors: Hiroshi Matsushita, Kanagawa-ken (JP); Kunihiro Mitsutake, Kanagawa-ken (JP); Yukihiro Ushiku, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 564 days.

(21) Appl. No.: 10/107,297

(22) Filed: Mar. 28, 2002

(65) Prior Publication Data

US 2003/0011376 A1    Jan. 16, 2003

(30) Foreign Application Priority Data

Mar. 29, 2001  (JP)  ............................ P2001-095479
Sep. 13, 2001  (JP)  ............................ P2001-278194

(51) Int. Cl.
*G01B 5/28* (2006.01)

(52) U.S. Cl. ...................................................... 702/35

(58) Field of Classification Search ................. 702/35, 702/84, 182, 184; 382/149; 700/110
See application file for complete search history.

(56) References Cited

U.S. PATENT DOCUMENTS 5,991,699 A    11/1999  Kulkarni et al.
6,016,278 A     1/2000  Tsutsui et al.
6,047,083 A *   4/2000  Mizuno ....................... 382/141
6,172,363 B1 *  1/2001  Shinada et al. .............. 250/310
6,324,481 B1 * 11/2001  Atchison et al. ............... 702/84
6,446,021 B1 *  9/2002  Schaeffer ..................... 702/118
6,466,895 B1 * 10/2002  Harvey et al. ............... 702/181
6,507,933 B1 *  1/2003  Kirsch et al. ................... 716/4
6,539,272 B1 *  3/2003  Ono et al. .................... 700/110
6,775,817 B2 *  8/2004  Ono et al. ...................... 716/21
2004/0026633 A1 * 2/2004  Gunji et al. ............... 250/492.1

FOREIGN PATENT DOCUMENTS

JP    2000-269276    9/2000

OTHER PUBLICATIONS

Co-pending Patent Application of: Kunihiro Mitsutake et al. Method, Apparatus, and Computer Program of Searching for Clustering Faults in Semiconductor Device Manufacturing U.S. Appl. No. 09/931,916, filed Aug. 20, 2001.

* cited by examiner

*Primary Examiner*—John Barlow
*Assistant Examiner*—Aditya Bhat
(74) *Attorney, Agent, or Firm*—Finnegan, Henderson, Farabow, Garrett & Dunner, L.L.P.

(57) ABSTRACT

An equipment for detecting faults in semiconductor integrated circuits includes a fault input unit to input fault information for the integrated circuits formed on a semiconductor wafer, a superimposing unit to superimpose the fault information with repeating units within the surface of the semiconductor wafer, and a first characteristic factor calculation unit to calculate a first characteristic factor showing a degree to which faults are repeated every repeating unit.

6 Claims, 37 Drawing Sheets

FIG.5
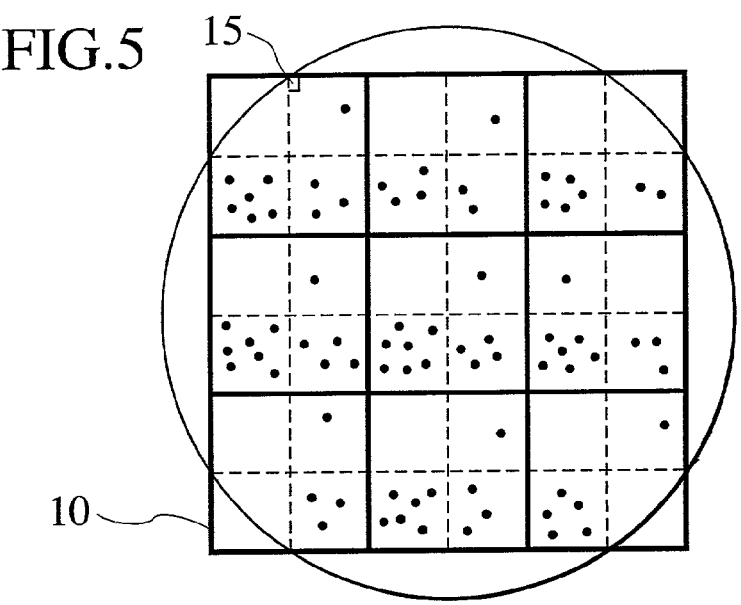
FIG.6
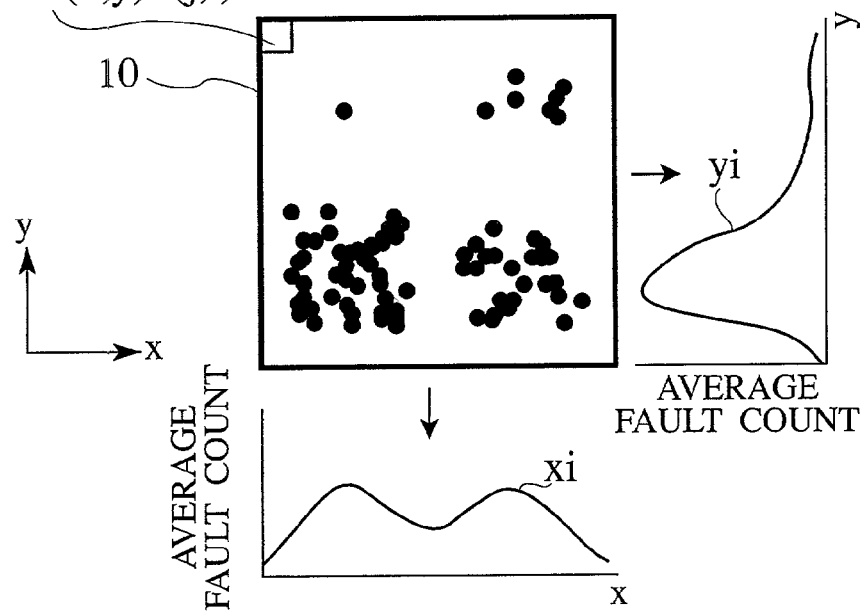
FIG.7
|  | LAG WIDTH | TRAVERSE COUNT | CORRELATION COEFFICIENT |
|---|---|---|---|
| x (SCAN) DIRECTION | 0.5 | 0 | 0.5 |
| y (SCAN) DIRECTION | 0.5 | 0.5 | 0 |

FIG.8
| FAULT DISTRIBUTION | 1st CHARACTERISTIC FACTOR IN x (SCAN) DIRECTION | 1st CHARACTERISTIC FACTOR IN y (SCAN) DIRECTION |
|---|---|---|
| 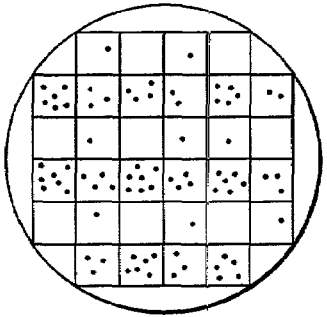 | 0.86 | 0.89 |
| 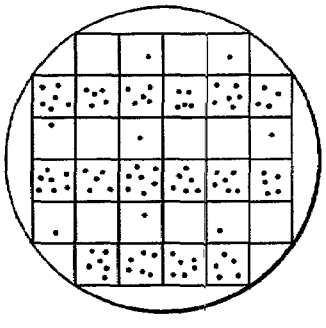 | 0.65 | 0.91 |
| 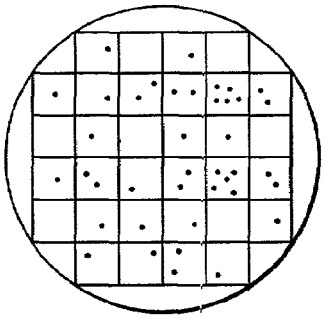 | 0.36 | 0.41 |
| 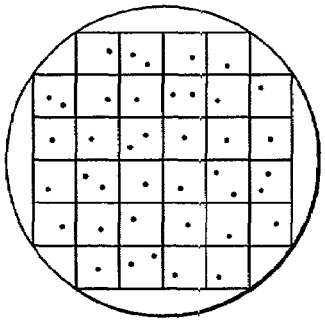 | 0.01 | 0.02 |

RADIAL POSITION

| FAULT DISTRIBUTION | 1st CHARACTERISTIC FACTOR |
|---|---|
|  | 0.92 |
|  | 0.43 |
|  | 0.03 |

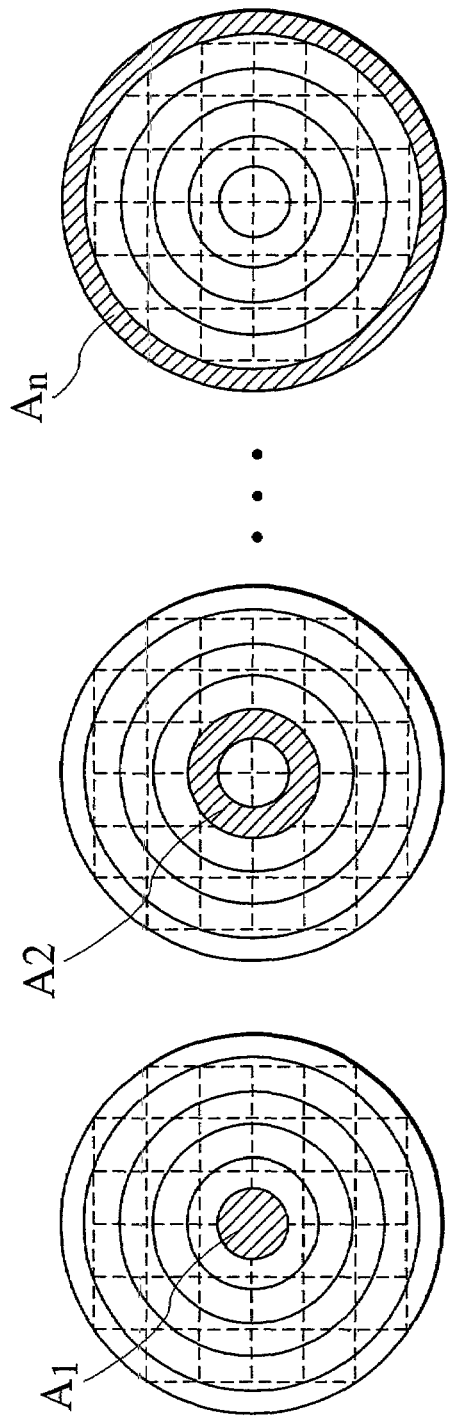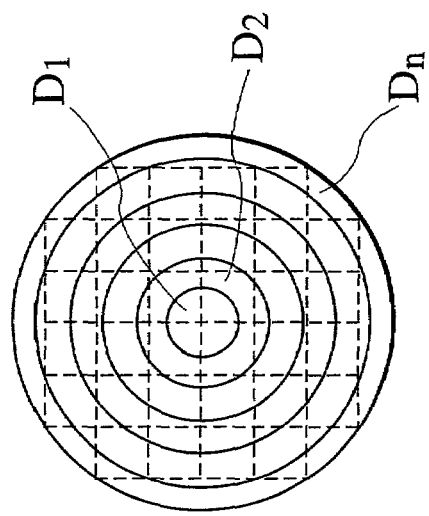

FIG.23
| WAFER ID | FAULT PATTERN | CLUSTERING FACTORS Wnb (%) | 1st CHARACTERISTIC FACTOR S (EXPOSURE CAUSED) | 1st CHARACTERISTIC FACTOR P (CIRCUMFERENTIAL FAULTS) | AUTO DETERMINATION RESULTS |
|---|---|---|---|---|---|
| A | 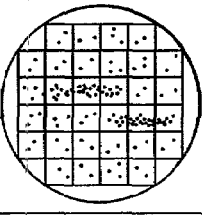 | 14 | 0.13 | 0.02 | UNKNOWN PATTERN |
| B | 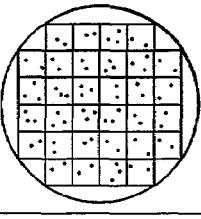 | 2 | 0.02 | 0.03 | RANDOM PATTERN |
| C | 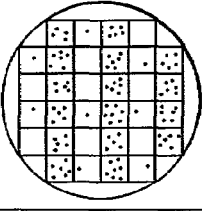 | 23 | 0.91 | 0.12 | LITHOGRAPHY-RELATED PATTERN |
| D | 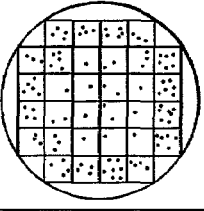 | 11 | 0.11 | 0.92 | CIRCUMFERENTIAL FAULT PATTERN |

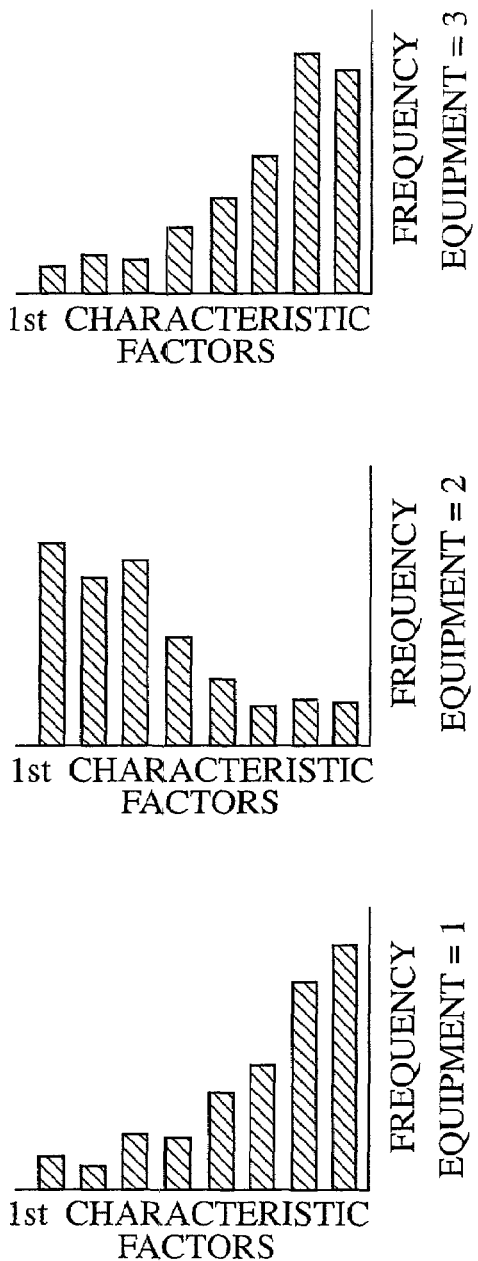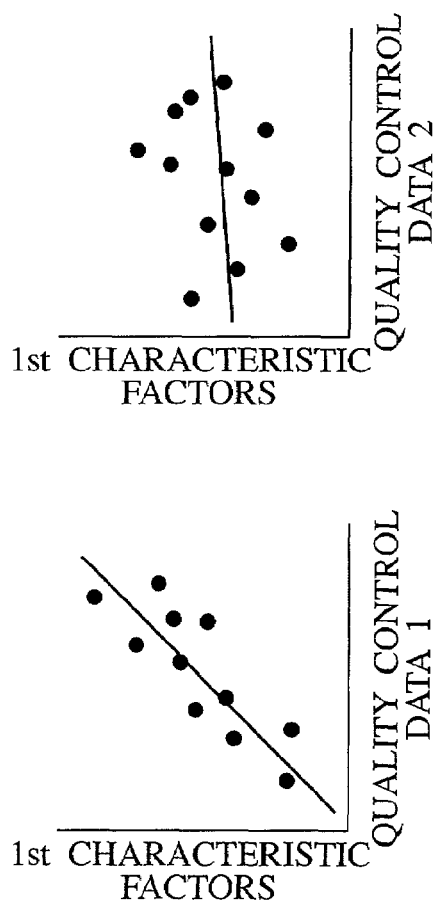

FIG.33
| FAULT DISTRIBUTION | Sx | Sy | Pr |
|---|---|---|---|
| 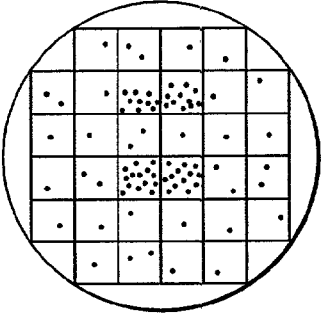 | 0.42 | 0.81 | 0.16 |
| 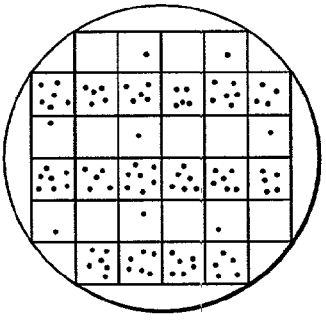 | 0.65 | 0.91 | 0.52 |
| 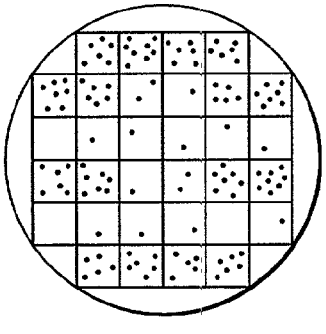 | 0.32 | 0.72 | 0.87 |

EQUIPMENT FOR AND METHOD OF DETECTING FAULTS IN SEMICONDUCTOR INTEGRATED CIRCUITS

CROSS REFERENCE TO RELATED APPLICATIONS

This application is based upon and claims the benefit of priority from the prior Japanese Patent Applications No. 2001-095479 filed on Mar. 29, 2001 and No. 2001-278194 filed on Sep. 13, 2001, the entire contents of which are incorporated herein by reference.

BACKGROUND OF THE INVENTION

1. Field of the Invention

The present invention relates to fault analysis of semiconductor integrated circuits. In particular, it is related to a method of detecting faults, which automatically classifies fault patterns from the tester information, and an equipment therefore.

2. Description of the Related Art

Recently, due to the scaling down of semiconductor devices, various processed-based faults have emerged. Results obtained from wafer testing, performed immediately after completion of wafer processing, can be used in process improvement strategy. For example, in the case of DRAM, the tester information can be represented upon the surface of a wafer as a mapping display (fail bit map). The tester information represents the position of fail bits. A determination is then made whether there exists a fault pattern particular to the semiconductor manufacturing equipment according to the distribution of fail bits. This determination has come to be performed by a person directly observing the fail bit map. Not only is this situation left wanting in terms of objectivity and quantitativity, it is difficult to check all of a mass-produced product.

Therefore, attempts have been made to perform this determination automatically with a computer. A fail bit map is input to a computer as an image or numeric data. The computer then automatically determines whether the fail bit distribution is singular (a single bit fault), line-shaped (a column or row), cross-shaped or planar-shaped. In addition, a computer is used to determine distribution within the wafer surface (e.g. center, on the orientation flat side).

There are many cases where fault patterns auto-detected in such a manner are included in the category of basic elements of fault patterns. In other words, in order to specify the manufacturing equipment responsible for a fault, the basic elements of a fault pattern must be compared with a historical database, or they must be compared with the fault patterns that emanate from a manufacturing equipment by human determination.

However, sensitivity is low with mere extraction of the basic elements of the fault pattern. In addition, if a fault pattern does not manifest the fact that yield is decreased, it means that it may be impossible to locate a manufacturing equipment that is causing the fault pattern to occur.

In addition, in the case where an automated extraction system is configured using a computer, fault patterns not presupposed can not be auto detected.

SUMMARY OF THE INVENTION

According to a first aspect of the present invention, an equipment for detecting faults in semiconductor integrated circuits includes a fault input unit to input a fault information for the semiconductor integrated circuits formed on a semiconductor wafer, a superimposing unit to superimpose the fault information with repeating units within the surface of the semiconductor wafer, and a first characteristic factor calculation unit to calculate a first characteristic factor showing a degree to which the faults are repeated every the repeating unit.

According to a second aspect of the present invention, a method of detecting faults in semiconductor integrated circuits includes inputting a fault information for the semiconductor integrated circuits formed on a semiconductor wafer, superimposing the fault information with repeating units within the surface of the semiconductor wafer, and calculating a first characteristic factor showing a degree to which the faults are repeated every the repeating unit.

BRIEF DESCRIPTION OF THE DRAWINGS

FIG. 5 is a plan view showing a method of superimposing the fault information with the exposure units;

FIG. 6 shows respective graphs for the fault count distribution superimposed with exposure units and the 1-D profiles of the fault count distribution;

FIG. 7 is a table representing the weighted average coefficients for calculating first characteristic factors;

FIG. 8 is a table showing respective fail bit distributions within wafer surfaces and respective lithography-related first characteristic factors for wafers with several fault patterns;

FIG. 19 is plan views showing a method of inputting the concentric unit information into the equipment of FIG. 16;

FIG. 20 is a plan view showing a method of outputting data superimposed with concentric units from the equipment of FIG. 16;

FIG. 23 is a table showing the respective fail bit distributions within wafer surfaces, clustering factors, characteristic factors, and automated determination results for wafers with several respective fault patterns;

FIG. 28 is graphs illustrating frequency distribution found by comparing first characteristic factors with the equipment history;

FIG. 29 is distribution diagram maps found by comparing first characteristic factors with quality control data;

FIG. 33 is a table showing the distribution of lithography-related faults within the surface of a wafer and the first characteristic factors (Sx, Sy, Pr);

DETAILED DESCRIPTION OF EMBODIMENTS

Figure 1:
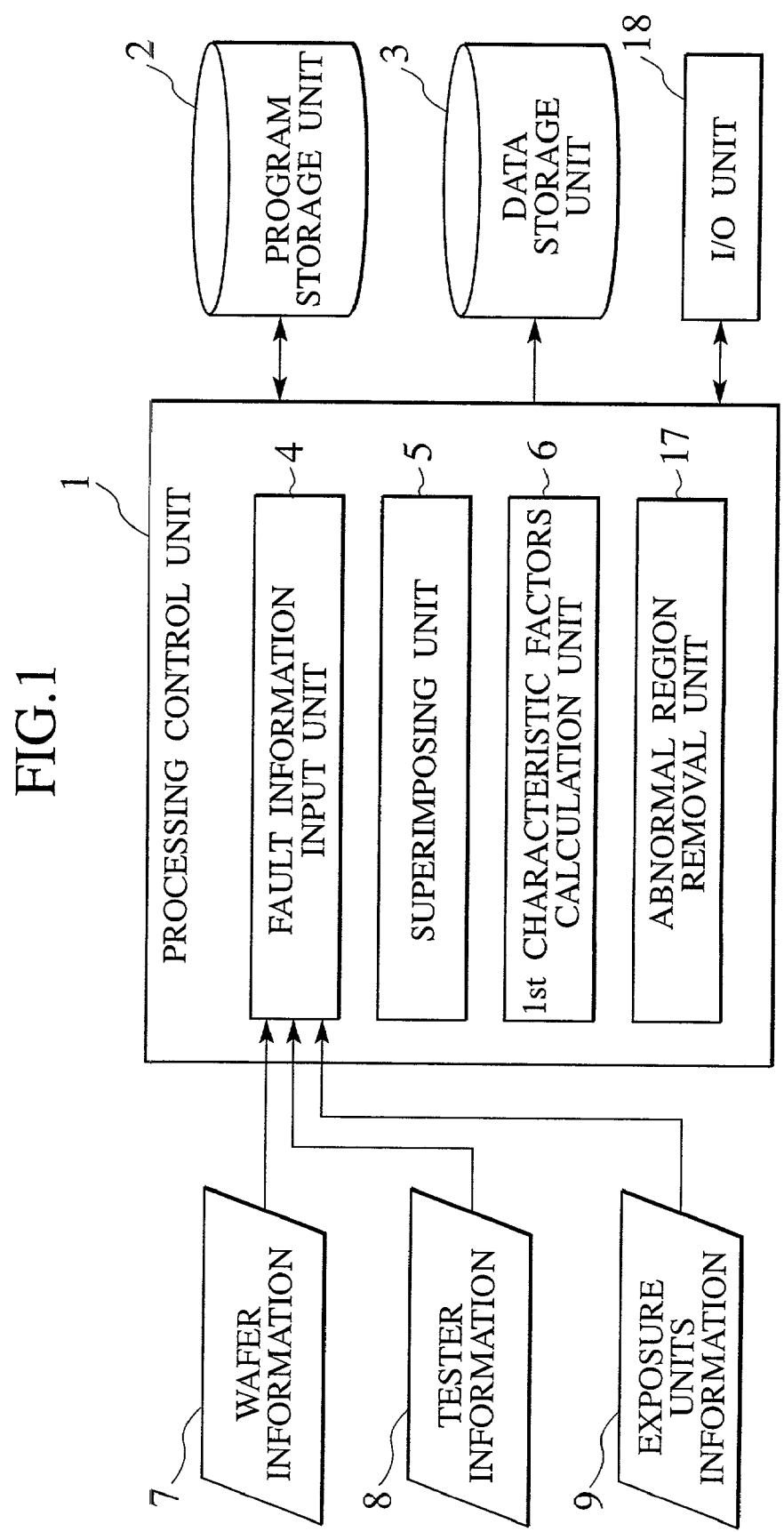
FIG. 1 is a block diagram showing an equipment for detecting faults in Semiconductor integrated circuits according to the first embodiment, which illustrates an equipment for auto detecting lithography related faults.

Various embodiments of the present invention will be described with reference to the accompanying drawings. It is to be noted that the same or similar reference numerals are applied to the same or similar parts and elements throughout the drawings, and the description of the same or similar parts and elements will be omitted or simplified.

(First Embodiment)

A method of detecting faults in semiconductor integrated circuits according to the first embodiment pertains to a method of auto detecting faults originating in the exposure process. To begin with, an equipment for detecting the faults will be explained with reference to FIG. 1.

In FIG. 1, the equipment for detecting the faults includes a processing control unit 1, a program storage unit 2, a data storage unit 3, and an I/O unit 18. The processing control unit 1 includes a fault information input unit 4, a superimposing unit 5, a first characteristic factors calculation unit 6, and an abnormal region removal unit 17. The fault information input unit 4 inputs a fault information of a semiconductor integrated circuit formed on a semiconductor wafer into the processing control unit 1. The superimposing unit 5 superimposes the fault information for every repeating unit across the surface of the semiconductor wafer. The first characteristic factors calculation unit 6 calculates the first characteristic factors from data obtained through the superimposing. The first characteristic factors show the degree to which faults have periodicity and/or regularity for every repeating unit. In the first embodiment, "repeating units" denotes exposure units.

The fault information includes a wafer information 7, a tester information 8, and a repeating unit information (an exposure unit information) 9. The wafer information 7 includes a number for identifying the wafer. The tester information 8 includes coordinates of each chip area upon the wafer surface and a fault count for every divisional unit. The fault count indicates where one chip area is divided into a plurality of divisional units. The exposure unit information 9 includes information related to exposure units or shot regions. The data storage unit 3 mainly stores the results for the fault pattern determination. More specifically, the data storage unit 3 stores the fault information, the first characteristic factors, and the determination result. The program storage unit 2 stores a computer program for the detecting faults.

The I/O unit 18 is a terminal used by an user when the user, instead of the input unit 4, imports the wafer information 7, the tester information 8, and the exposure unit information 9 into the processing control unit 1. The I/O unit 18 is connected to the processing control unit 1. The I/O unit 18 may be a keyboard, mouse, light-pen, printer, floppy disk drive, or any other else.

A method of detecting the faults using the equipment shown in FIG. 1 will be explained with reference to FIG. 2 to 8.

Figure 2:
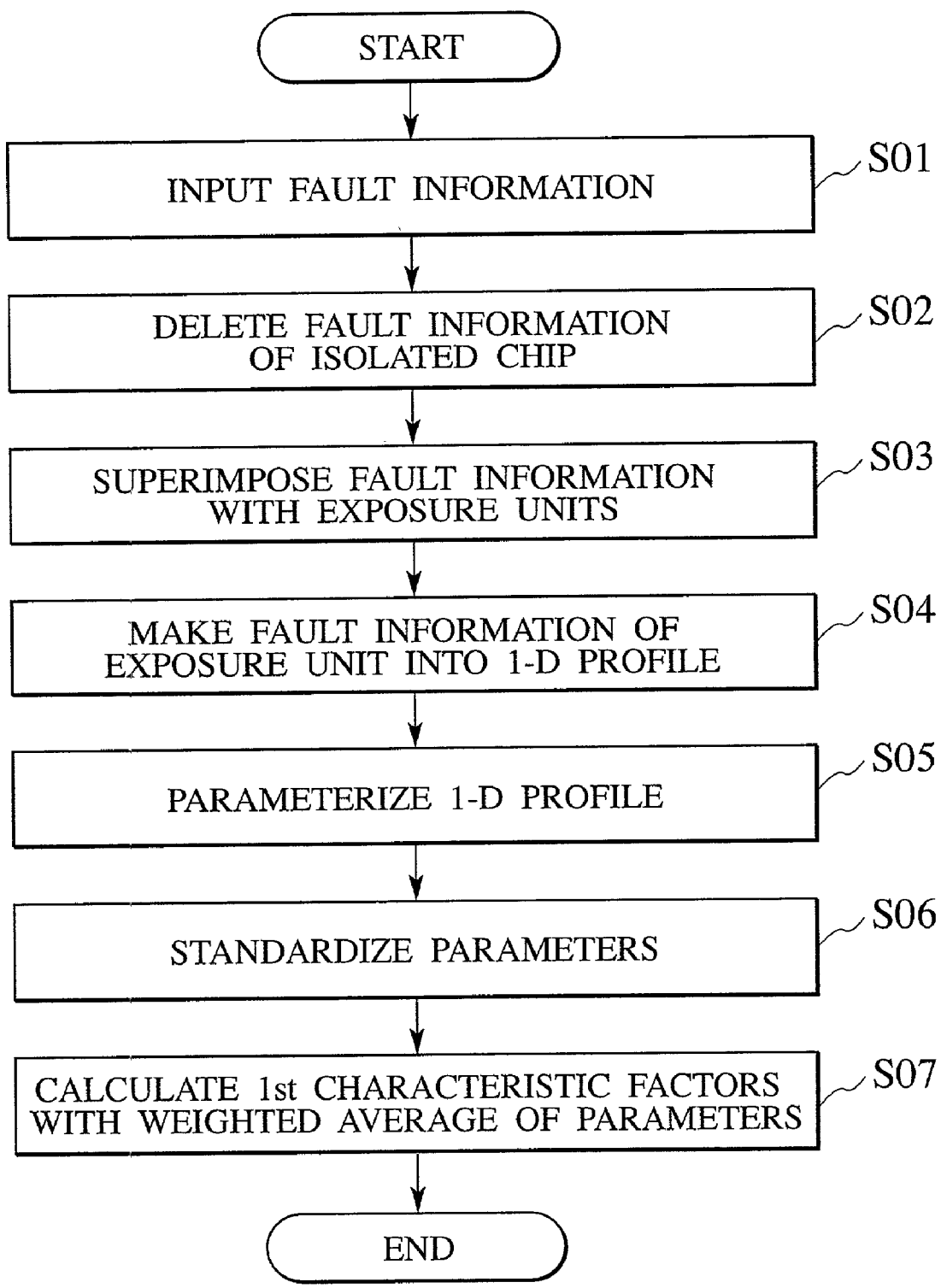
FIG. 2 is a flowchart illustrating a method of detecting faults in semiconductor integrated circuits according to the first embodiment.

(I) In FIG. 2, stage S01 imports the fault information in the semiconductor integrated circuits into the processing control unit 1.

Figure 3:
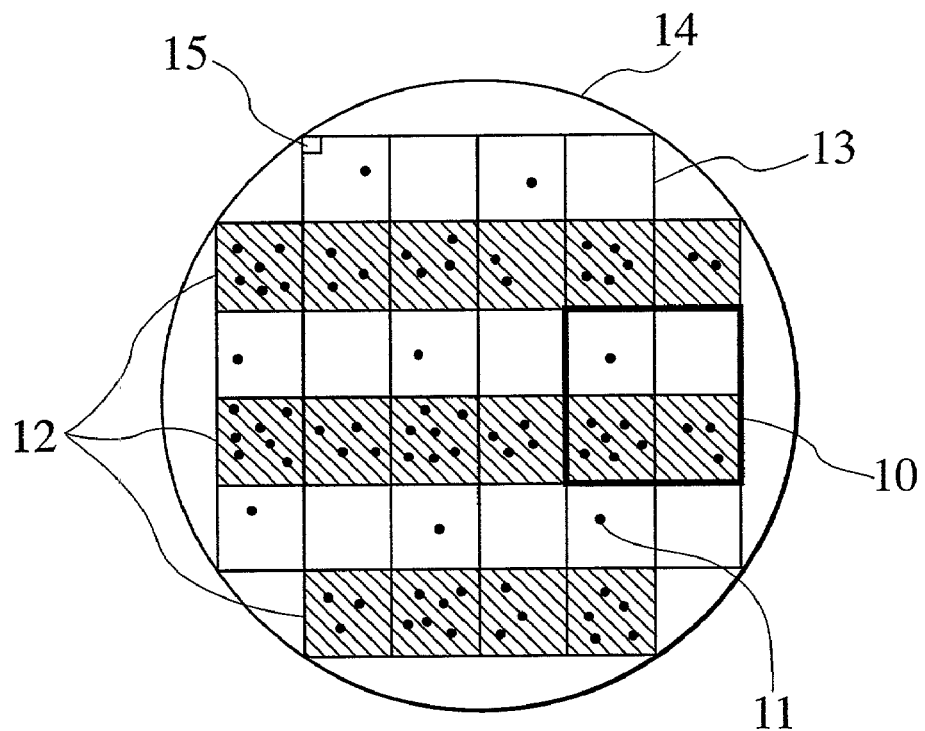
FIG. 3 is a plan view showing fail bit locations occurring in DRAM following wafer process completion according to the first embodiment.

For example, as shown in FIG. 3, fail bits 11 may be distributed in regular bands 12 in DRAM formed upon the semiconductor wafer 14. The black dots represent the position of fail bits 11. The semiconductor wafer 14 includes a plurality of chip areas 13 disposed in a matrix. Exposure unit 10 represents an exposure pattern burn unit. There are 4 chip areas 13 included in one exposure unit 10. The distribution of fail bits 11 (the chip areas 12 of which oblique line is appended.) are repeated regularly at every exposure unit 10. Accordingly, it is estimated that the fail bits 11 are lithography-related faults. In such a situation, the fault information input unit 4 imports the exposure unit information 9 into the processing control unit 1 as the repeating unit information.

The fault information, imported into the fault information input unit 4, denotes the single bit unit information for the entire wafer surface. However, the fault pattern exists in the order of the chip area size. Accordingly, the information content of the fault information may be reduced without any problem provided that the shape of the fault pattern is not damaged. Therefore, the first embodiment splits one chip area 13 into a plurality of divisional units 15. One divisional unit 15 includes a plurality of bits. The fail bit count for every divisional unit 15 is then found, and the lithography-related faults are automatically extracted from the fail bit count for every divisional unit 15.

(II) Stage S02 deletes the fault information of isolated chip areas. For example, the isolated chip areas have a total fault count which is more prominent than the total fault count within the surrounding chip areas. In other words, if the total fault count in a predetermined area is larger than the surrounding position information, the predetermined area is determined to have the above-mentioned abnormal position information. The isolated chip areas are then excluded from the objects to be subjected to the subsequent processing.

Figure 4:
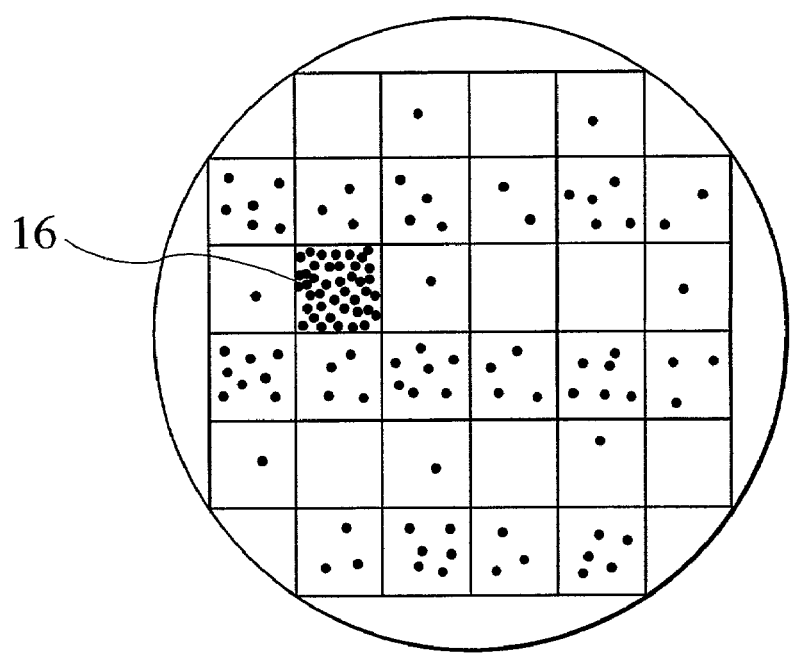
FIG. 4 is a plan view showing fault region determined to be an abnormal region vis-à-vis the independent repeating units of a fault pattern.

More specifically, as shown in FIG. 4, there are cases where an isolated chip area 16 develops, with a fault count that stands out in comparison with the surrounding chip areas. Since the isolated chip area 16 deviates from the lithography-related faults, the isolated chip area 16 interferes with the auto detection. The isolated chip area 16 is then excluded from the objects to be subjected to subsequent processing before the superimposing processing is begun.

The total fault count for every chip area is given as Ci (wherein i =1, 2, . . . , n, and n represents the chip area count). The maximum value of Ci is given as Cmax. In addition, Cmed denotes the median of Ci. In addition, the total fault count of the eight chip areas, positioned around a chip area having Cmax, is given as Cj (wherein j=1, 2, . . . 8). When the conditional expression denoted as expressions (1a) and (1b) are satisfied, the chip area having Cmax is determined to be an isolated chip area.

$$Cmax/Cmed>100, \text{ and} \tag{1a}$$

$$Cmax/Cj>10(j=1, 2, \ldots, 8) \tag{1b}$$

Regions, which are the exception in comparison with a fault pattern repeating every exposure unit 10, are not limited to isolated chip areas. The regions mentioned above can be considered regions which disrupt the periodicity of the faults generally wanted to be detected. Every time the existence of such a region is confirmed, it is followed by the processing to exclude the region.

(III) Stage S03 superimposes the fault information for each exposure unit 10 within the wafer surface in order to highlight the periodicity of the exposure unit 10.

More specifically, as shown in FIG. 5, the wafer surface is partitioned into the exposure units 10. Then, the respective fault counts of the divisional units 15, which correspond with each exposure unit 10, are added together. In other words, fault counts of the divisional units 15, which are in locations translationally adjoining each other, are added together. In addition, the fault count for each divisional units 15 within an exposure unit 10 are counted. The operation mentioned above is performed on all of the exposure units 10. Thereafter, the fault count calculated for every divisional unit 15 is divided by the number of the superimposed exposure units 10. The divided results can be seen as the average value of the fault count in each divisional unit 15. The superimposing processing mentioned above is performed to exclude chip areas having the missing fault information and chip areas missed out at the wafer ends.

As shown in FIG. 6, the average fault count for every divisional unit 15 within exposure unit 10 can be obtained from the results of the superimposing processing.

(IV) As shown in FIG. 6, stage S04 makes the superimposed fault information into a 1-D profile for the respective x- and y-direction, which are perpendicular with each other. 1-D profile yi (where i=1, 2, . . . , ny) in the y-direction may be found from the following expression (2). "ny" denotes the division count of the exposure unit 10 in the y-direction.

$$y_i = \left(\sum_{j=1}^{nx} f(j, i)\right) / nx \tag{2}$$

f(j, i) denotes the average fault count of divisional unit 15 which is positioned at (x, y)=(j, i) of exposure unit 10. "nx" denotes the division count of the exposure units 15 in the x-direction. 1-D profile xi in the x-direction can be found in the same way by replacing y in expression (2) with x. If faults have a periodicity of every exposure unit 10, some sort of regularity is found in the y-direction or x-direction 1-D profile (yi, xi).

(V) Stage S05 finds the following four parameters (a) to (d) from the 1-D profile (yi, xi).

(a) autocorrelation function Rac(k)
(b) lag width L0
(c) crossing frequency
(d) cosine correlation coefficient Autocorrelation function Rac(k), which is a function of shift (lag) k, shows the correlation between the 1-D profile and a shifted 1-D profile along y-axis or x-axis. Autocorrelation function Rac(k) is described forthwith.

To begin with, a 1-D profile (yi, xi) is expressed as a time sequence $\{t1, t2, \ldots, tn\}$ along the y-axis or x-axis. The average value $\mu$ of the 1-D profile (yi, xi) is expressed as expression (3).

$$\mu = (1/N) \sum_{i=1}^{N} t_i \quad (3)$$

The auto-covariance $C_k$ is then calculated from the average value $\mu$ using expression (4).

$$C_k = (1/N) \sum_{i=k+1}^{N} (t_i - \mu)(t_{i-k} - \mu) \quad (4)$$

Finally, the autocorrelation function Rac(k) is calculated from the auto covariance $C_k$ using expression (5).

$$Rac(k) = C_k/Co \quad (5)$$

The lag width L0 shows the value of k where Rac(k)=0. Here, a portion of the autocorrelation function Rac(k) is approximated with a linear equation calculating the lag width L0. More specifically, the point where Rac (0)=1 and the point where Rac(k)=0.5 can be connected by a straight line. This straight line makes lag width L0 the value of k at the time where Rac(k)=0.

The crossing frequency shows the number of times when the 1-D profile crosses the average value $\mu$ shown in expression (3).

The cosine correlation coefficient shows the correlation coefficient between the frequency component of the 1-D profile and the cosine function. More specifically, the 1-D profile is approximated as a linear equation. The 1-D profile is then represented as a sum of the linear (equation) component and the residual components. It is correspondent to dividing the 1-D profile into the trend component and the periodic component. The polynomial of the lowest order, which is sufficient in approximating the periodic component of the 1-D profile, is obtained. Then, the correlation coefficient between the cosine function closest to this polynomial and the periodic component of the 1-D profile, are calculated. The correlation coefficient denotes the cosine correlation coefficient.

The lowest order of the polynomial is determined by following. Starting with the tenth order, the polynomial order is incrementally decreased. Then, the decreasing rate of the relative correlation coefficient between the polynomial and the periodic component of the 1-D profile is obtained. The order, just before the decreasing rate of the correlation coefficient exceeds 10% for the first time, is made to be the lowest order of the polynomial. Note that the correlation coefficient for the tenth order polynomial is given as 1.

k, in which the Rac(k) becomes zero for the first time, may be made to be the lag width L0. Alternatively, by approximating Rac(k) with a polynomial, lag width L0 may be found from the point where the polynomial becomes zero. In addition, it may be made to be the crossing frequency that the median of the 1-D profile and the intermediate value between the minimum value and maximum value of the 1-D profile.

(VI) Stage S06 standardizes each parameter (b) to (d) at a numerical value from 0 to 1. Each parameter (b) to (d) approaches 1, and shows the condition that the lithography-related faults occur frequently. Since the autocorrelation function Rac(k) exists within the lag width L0, the Rac(k) is not used as a standardized parameter.

The regularity appears more in the 1-D profile, as the value of the lag width L0 is bigger. In other words, the lag width L0 shows the existence of many lithography-related faults. Therefore, the lag width L0 is given as 1 in the case where the divisional count of the exposure units in the either the x or y direction reaches 40% or higher; the lag width L0 is given as 0 in the case where the lag width L0 is 1 or less; and there between it is linearly interpolated.

The irregularity appears more in the 1-D profile, as the value of the crossing frequency is bigger. In other words, the crossing frequency shows there to be few lithography-related faults. Therefore, the crossing frequency is given as 0 in the case where the divisional count of the exposure units in the either the x or y direction reaches 30% or higher; the crossing frequency is given as 1 in the case where the crossing frequency is 1 or less; and there between it is linearly interpolated.

The regularity appears more in the 1-D profile, as the value of the cosine correlation coefficient approaches 1. Therefore, the value of a cosine correlation coefficient of at least 0 but no greater than 1 can be used as is, and a cosine correlation coefficient less than 0 is replaced with 0.

Note that it is not always necessary to limit the parameter standardization to between 0 and 1. The parameter standardization may be made to correspond to consecutive closed intervals on a number line. In addition, if more lithography-related faults exist, it is acceptable for the values to be standardized so as to be made smaller. In this case, the determination conditions for whether or not a failure pattern exists, as described below, may be reversed.

(VII) Stage S07 calculates the first characteristic factors in both the x and y directions of the exposure units by using the weighted average of the each standardized parameter. The weighted average of each parameter is determined taking the exposure mode into consideration. The exposure mode includes a scanning exposure mode in which scanning is performed while synchronously moving the reticle and wafer. In FIG. 6, the x-direction corresponds to the scan direction. It is considered that variation in the fault count may occur in the scan direction depending on stability during scanning. The variation in the fault count is approximated with a cosine function.

On the other hand, in the slit direction (y direction), which is perpendicular to the scan direction, there exists polarization of the fault count due to distortions in the optical unit. The crossing frequency is considered as representing such a polarized condition. The coefficients of the weighted average of each parameter shown in FIG. 7 are set considering the points mentioned above. The first characteristic factors in both the x and y directions of the exposure unit are calculated.

As mentioned above, the first characteristic factors, which show the degree of lithography-related faults, can be found. As shown in FIG. 8, respective wafers, each having faults repeating at every exposure unit, have the first characteristic factors with a large value close to 1. A wafer with random fault distribution has a first characteristic factor with a small value close to 0. Determination of whether there exist lithography-related faults is made with a threshold value of approximately 0.4. In addition, due to the fault patterns being different in the scan direction and slit direction, it is also understood that the magnitudes of the first characteristic factors in each direction differ.

The tester information 8 may include chip area coordinates of the fail bits and the address information. In this case, logical summation may be used for the superimposing of the exposure units. On the other hand, in the case where logical multiplication is taken, faults common to the mask can be detected.

It is noted that the method of detecting faults according to the first embodiment may be represented by a series of processing or operations linked in a time sequence, or a 'procedure'. Accordingly, it is possible to configure the method as a computer program that specifies a plurality of functions for a processor within a computer system to carry out. As a result, it is possible to execute the method using a computer system. In addition, this computer program can be recorded (saved) on computer-readable storage media. This storage media is read by a computer system to execute the computer program. Accordingly, a computer system can control the method of detecting faults. Here, the storage media may comprise memory media capable of being stored with a program such as semiconductor memory, magnetic disks, optical disks, or magnetic tape.

Figure 9:
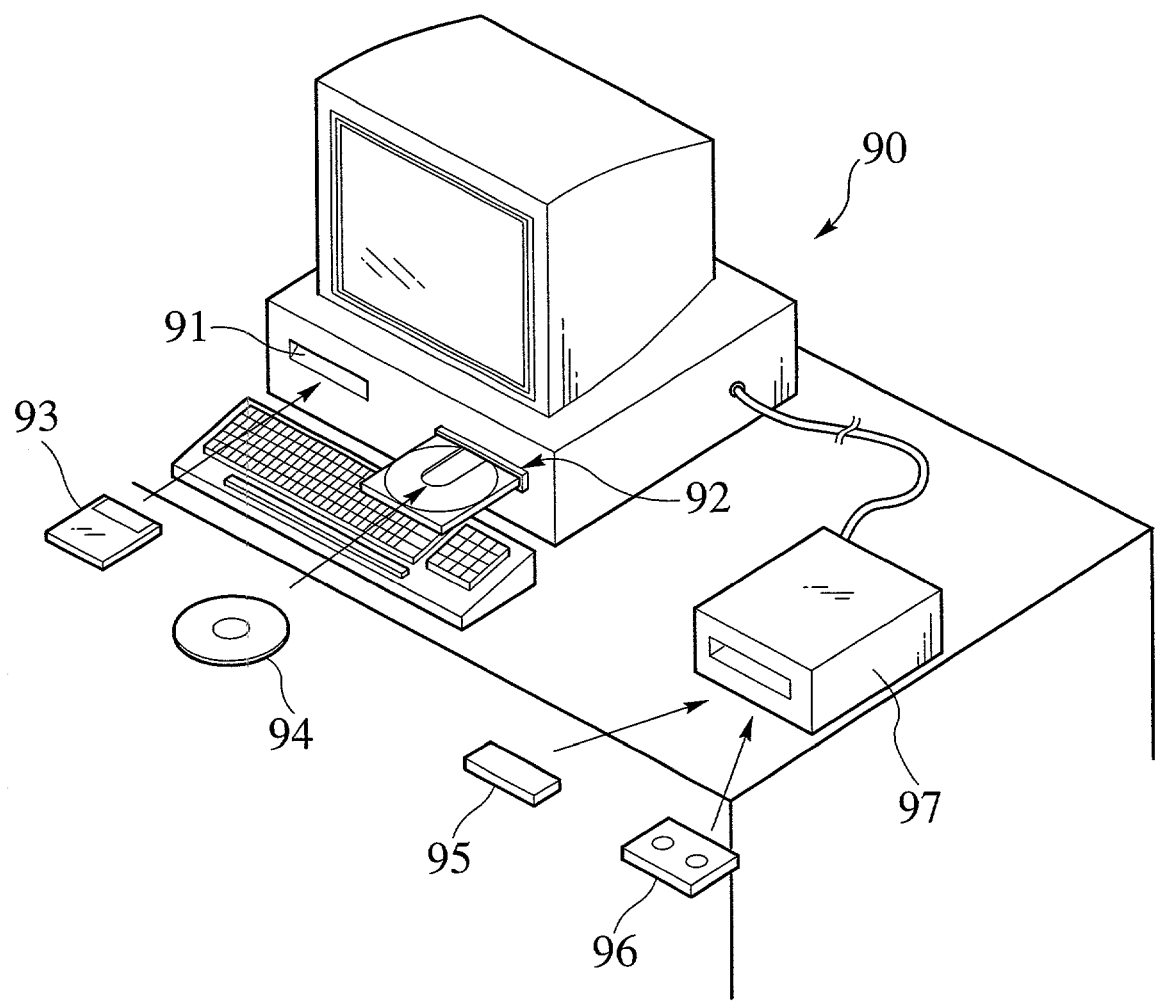
FIG. 9 is an outline view illustrating a computer system as an example of an equipment for detecting faults according to the first embodiment.

As shown in FIG. 9, a floppy disk drive 91, and a CD-ROM drive 92 are disposed on the front panel of the main unit of the computer system 90. A floppy disk 93 and a CD-ROM 94 are inserted into the respective drives thereof, and a predetermined read operation is performed so as to install the computer program stored on the respective storage media into the system. Moreover, a predetermined drive 97 may be connected to the computer system 90 to allow, for example, use of semiconductor memory such as that used in game packs as a ROM 95, or a magnetic tape as cassette tape 96.

As described above, according to the first embodiment, the existence of the lithography-related faults can be auto detected.

(Second Embodiment)

Figure 12:
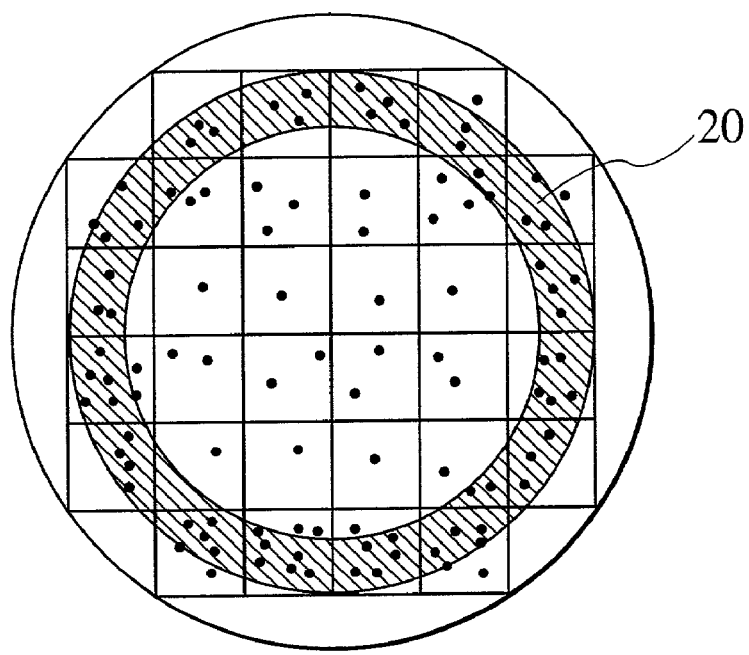
FIG. 12 is a plan view showing a fail bit location occurring in DRAM following wafer process completion according to the second embodiment, which illustrates the fault pattern of a wafer with circumferential faults.

In the second embodiment, an equipment for and a method of detecting faults, which develop concentrated around the outer circumference of the wafer, will be described. More specifically, as shown in FIG. 12, many faults 20 have developed near the outer circumference of the wafer. Accordingly, it is deduced that the cause of the faults is different from that in the first embodiment. Therefore, using the fault information for every divisional unit, the fault region with a greater distribution around the wafer circumference is auto extracted.

Figure 10:
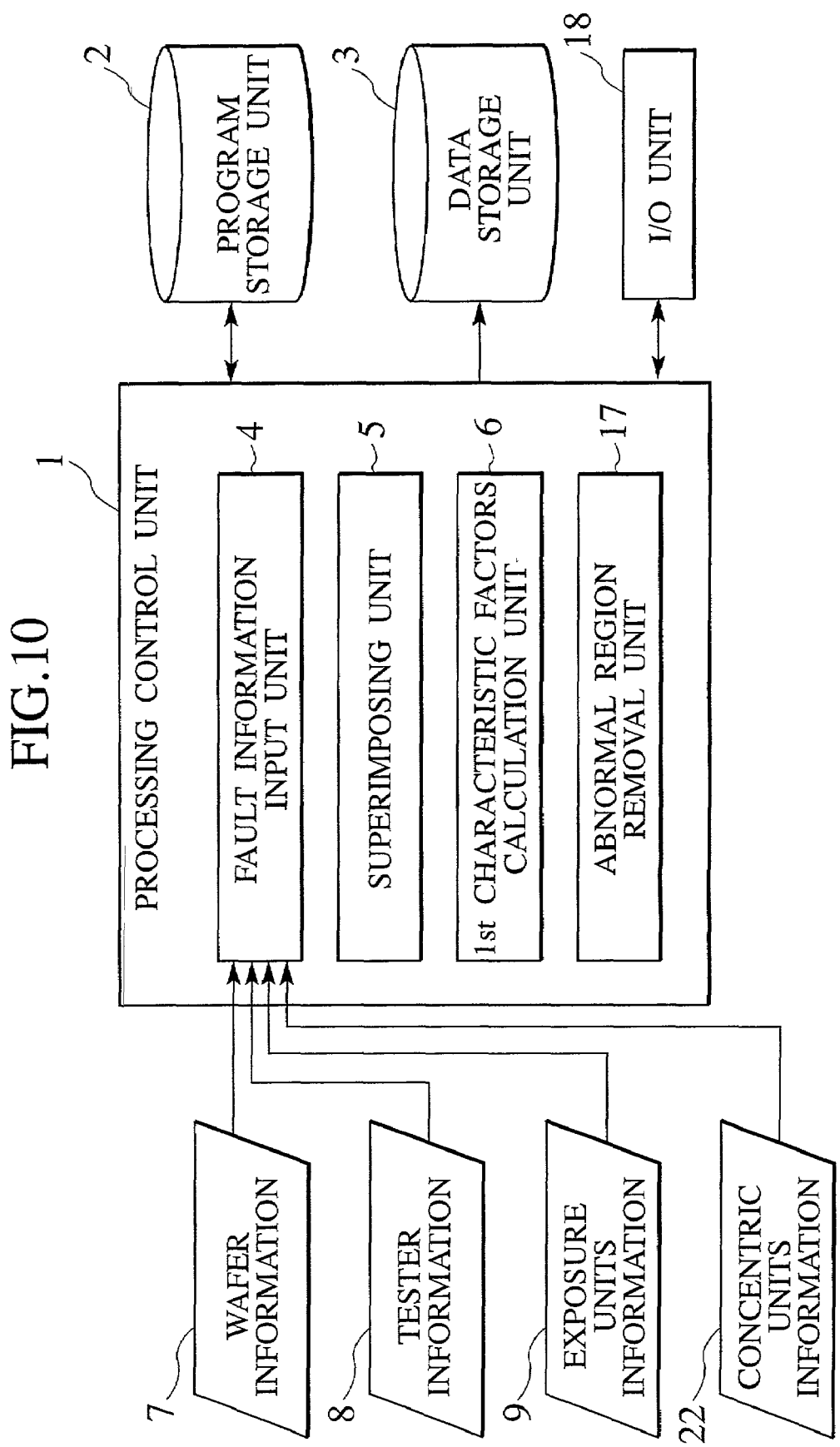
FIG. 10 is a block diagram showing an equipment for detecting circumferential faults and lithography-related faults according to the second embodiment.

As shown in FIG. 10, the equipment for detecting faults according to the second embodiment has almost the same configuration as the equipment shown in FIG. 1. However, when compared with the equipment shown in FIG. 1, it differs in that the fault information input unit 4 imports a concentric unit information 22. The concentric unit information 22 is the information related to the concentrically repeating units. In addition, a computer program for the method of detecting faults is stored in the program storage unit 2.

Figure 11:
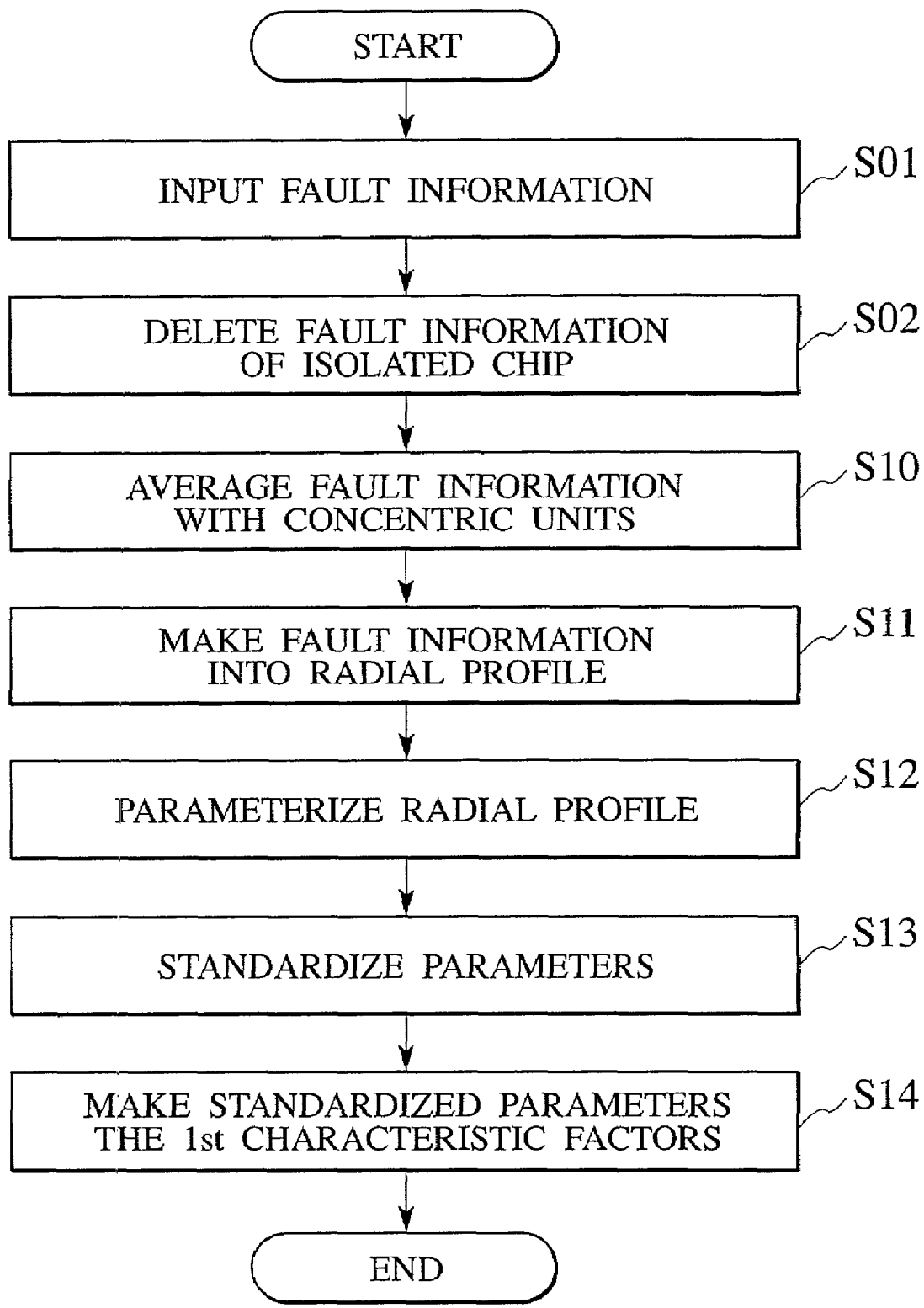
FIG. 11 is a flowchart illustrating a method of detecting circumferential faults according to the second embodiment.

A method of detecting faults according to the second embodiment will be explained with reference to FIG. 11.

(I) To begin with, stage S01 imports the fault information into the processing control unit 1. Stage S02 deletes the fault information of the isolated chip areas which may impede auto detection.

Figure 13:
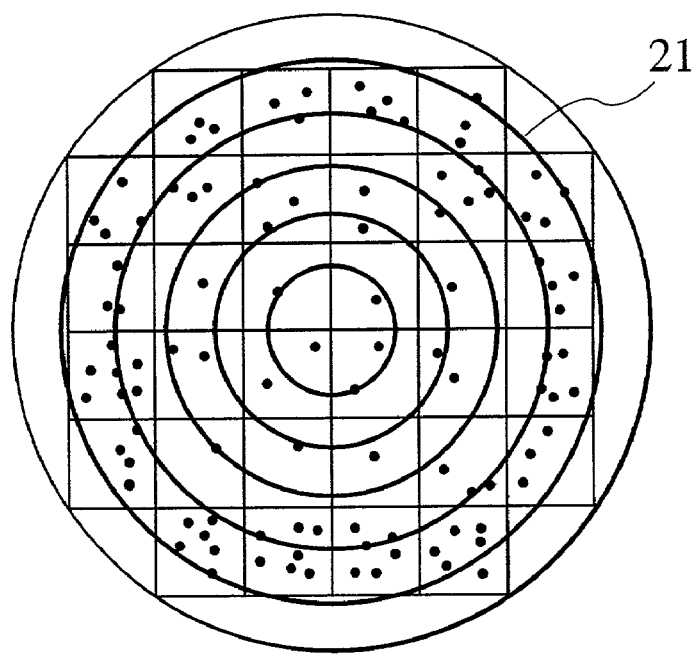
FIG. 13 is a plan view showing a method of superimposing the fault information with the concentric units.

(II) As shown in FIG. 13, stage S10 sets concentrically repeating units (hereafter referred to as 'concentric units') 21. The concentric units 21 show the concentric ring-shaped regions surrounding the wafer center. The average value of the fault count within each concentric unit 21 is then found.

Figures 14, 15:
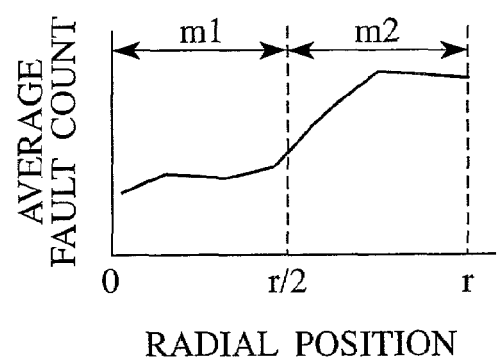
FIG. 14 is a graph showing radial fault distribution within a wafer surface, which illustrates distribution of fault counts for a wafer with circumferential faults.
FIG. 15 is a table showing respective fail bit distributions within wafer surfaces and corresponding first characteristic factor for circumferential faults, for wafers with several fault patterns.

(III) Stage S11 profiles the fault count within each concentric unit 21 as a function of the wafer radius (r). As a result of the profiling, as shown in FIG. 14, the radial distribution of the fault count can be obtained.

(IV) Stage S12 parameterizes the fault count radial distribution. As shown in FIG. 14, the average fault count of an inside region is given as m1, and the average fault count of an outside region is given as m2. The inside region has a distance of at least 0 but less than r/2 from the wafer center. The outside region has a distance of equal to or greater than r/2 but less than r. Parameter k is represented as k=m2/m1.

(V) Stage S13 standardizes parameter k. More specifically, the first characteristic factor is given as 0 in the case where parameter k is less than 1; the first characteristic factor is given as 1 in the case where parameter k is 2 or greater; and there between it is linearly interpolated. Then, in stage S14, the standardized parameter k is made to be the first characteristic factor of the circumferential faults.

As mentioned above, the first characteristic factors, which are for extraction of the circumferential faults, can be found. As shown in FIG. 15, the wafer clearly having a greater fault distribution at the wafer circumference has a first characteristic factor with a large value close to 1. On the other hand, the wafer having random fault distribution has a first characteristic factor with a small value close to 0.

As described above, according to the second embodiment, the existence of circumferential faults can be auto detected.

(Third Embodiment)

In the third embodiment, an equipment for and a method of detecting unknown patterns, which have not been presupposed, will be explained. In addition, a method of registering a detected unknown pattern as a new fault pattern will be explained.

Figure 16:
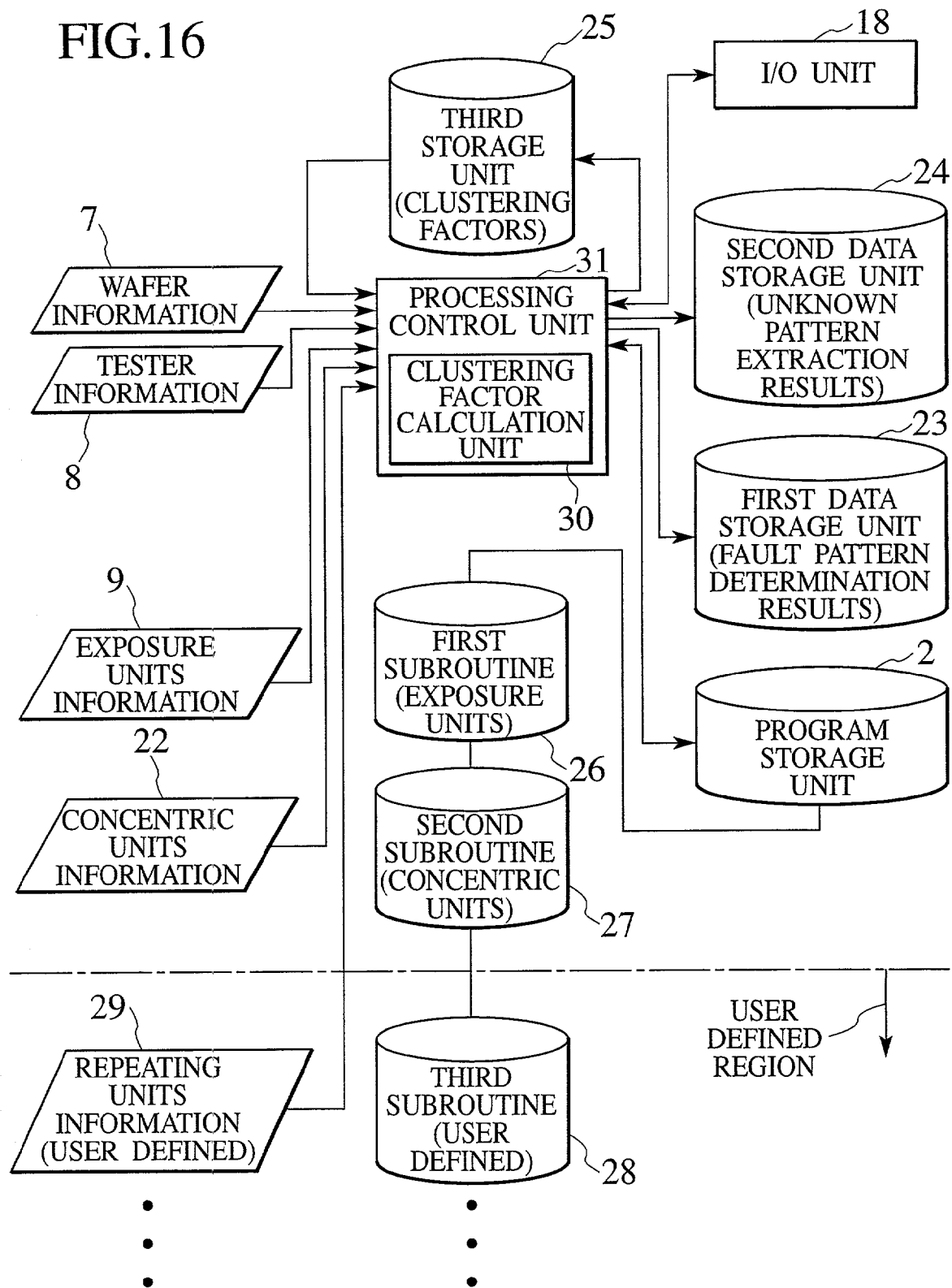
FIG. 16 is a block diagram showing an equipment for detecting unknown fault patterns, which were not presupposed, according to the third embodiment.

As shown in FIG. 16, an equipment for detecting faults according to the third embodiment includes a processing control unit 31, a program storage unit 2, first to third data storage units 23 to 25, and an I/O unit 18. Besides function block (4 to 6 and 17) shown in FIG. 1, processing control unit 31 further includes a clustering factors calculation unit 30. The clustering factors calculation unit 30 calculates second characteristic factors from the input tester information 8. The second characteristic factors denote clustering factors.

The first data storage unit 23 is equivalent to the data storage unit 3 shown in FIG. 1, and stores data relating to the fault pattern determination results. The second data storage unit 24 stores data relating to extraction results for unknown patterns that have not been presupposed by the user. The third data storage unit 25 stores clustering factors, which show the magnitude of fault polarization within the wafer surface.

The program storage unit 2 is connected to first to third subroutines 26 to 28. The first sub-routine 26 includes a computer program for detecting faults having the exposure unit periodicity shown in FIG. 3. The second sub-routine 27 includes a computer program for detecting fault patterns having the circumferential faults shown in FIG. 12. The third sub-routine 28 includes a computer program for detecting faults that are arbitrarily set by the user. A fault information input unit 4 (not shown in FIG. 16) imports the repeating unit information 29, which the user defines, in addition to the wafer information 7, the tester information 8, the exposure unit information 9, and the concentric unit information 22.

When the unknown pattern is registered as a new fault pattern in the second data storage unit 24, the user can define the repeating unit information 29 to be used for detecting the new fault pattern. In addition, it is possible for the user to the set third sub-routine 28 as a first characteristic factor calculation program to be used for detecting the new fault pattern, and add the third sub-routine 28 to the equipment shown in FIG. 16. By repeating the user-defining procedure, it is possible to increase the number of fault patterns that can be auto determined.

In order to simplify the new fault pattern registration, the equipment for detecting faults shown in FIG. 16 has formats of the repeating unit information (9, 22, 29). The formats are integrated into expressions (6)–(8).

$$\text{repeating unit information} = \{A, Cal\} \quad (6)$$

$$\text{repeating units } A = \{A1, A2, \ldots, An\} \quad (7)$$

$$A1 = \{J11, J12, \ldots, J1m1\}$$

$$A2 = \{J21, J22, \ldots, J2m2\}$$

$$An = \{Jn1, Jn2, \ldots, Jnmn\} \quad (8)$$

Here, the repeating units A represent a set of all repeating units covering the entire wafer surface. Ai, which is a component of A, represents a set of the divisional units upon the wafer which are to be subjected to superimposition. Jij represents the position of the j-th divisional unit belonging to Ai. For example, in the case where the tester information 8 is given as the fault information in respect to coordinates of a chip and coordinates within the chip area, Jij is configured with the same mode of the chip coordinates and coordinates within the chip area.

Cal designates the calculation method used during the superimposing processing. Averaging, logical addition, or logical multiplication can be used for the calculation method. The processing control unit 31 references {A, Cal}, employ calculation Cal for all divisional unit fault information belonging to Ai, and output the superimposing results Di. The processing mentioned above is performed for all Ai. More, specifically, the superimposing results are output in the format of the following expression (9).

$$D = \{D1, D2, \ldots, Dn\} \quad (9)$$

The superimposing processing, database processing, and clustering factor calculation function are written within the program storage unit 2. The programs calculating the first characteristic factors for the registered fault patterns are independently written in the first to third sub-routines (26 to 28). It is possible for the user to store the programs calculating each first characteristic factor of the superimposing processing results D in the sub-routine format. Namely, it is possible to input the superimposing processing results D, and have the first characteristic factor set C output as shown in expression (10).

$$C = \{C1, C2, \ldots, Cn\} \quad (10)$$

The first characteristic factors may be scalar amounts, or the first characteristic factors may be L-dimensional vectors. In addition, the determination result of whether a pattern exists may be added to the returned values.

Figure 17:
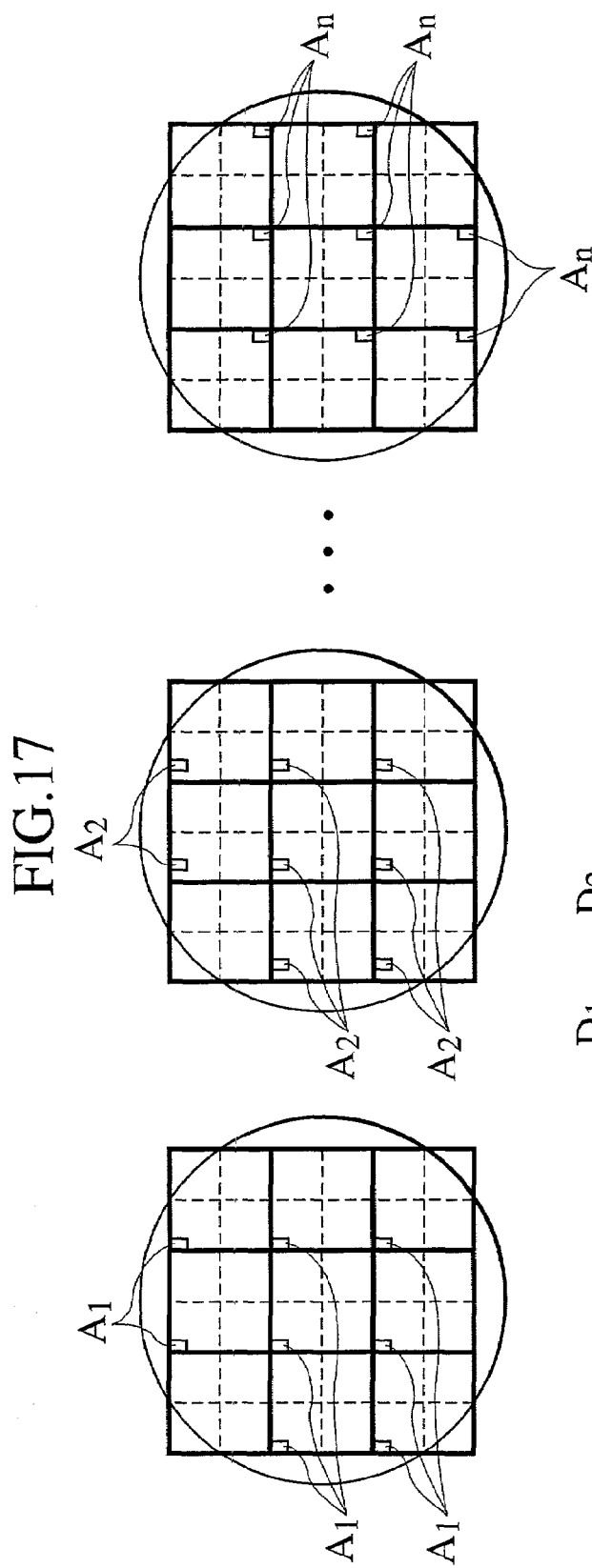
FIG. 17 is plan views showing a method of inputting the exposure unit information into the equipment of FIG. 16.
Figure 18:
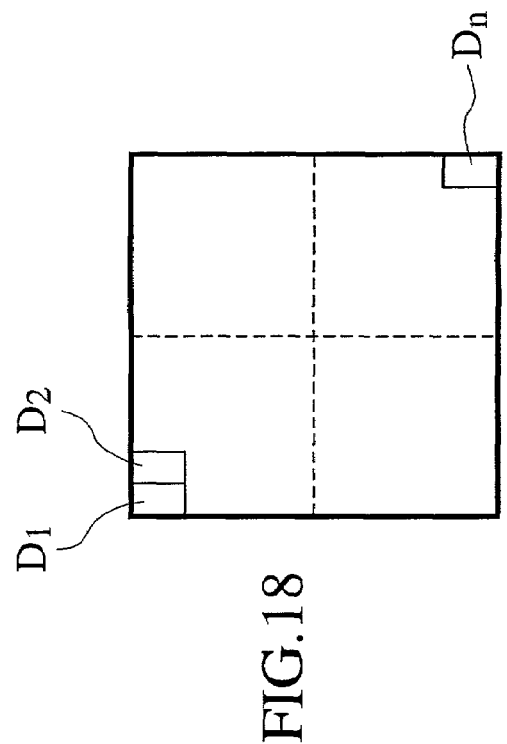
FIG. 18 is a plan view showing a method of outputting data superimposed with exposure units from the equipment of FIG. 16.

The processing control unit 31 may automatically systematize the returned values C from the user-created third sub-routine 28, and the determination result of whether a pattern exists. More specifically, in the case of the lithography-related faults, as shown in FIG. 17, each adjoining divisional unit is given as Ai. 'Averaging' is then designated as calculation method Cal during the superimposition processing. In response to the 'averaging', as shown in FIG. 18, the processing control unit 31 outputs an average fault count $D_i$ for each divisional unit within the exposure unit. Then, using the first sub-routine 26, the first characteristic factor $C_i$ is calculated from the average fault count $D_i$. The calculated result is written into the first data storage unit 23.

In the case of the circumferential faults, as shown in FIG. 19, each ring-shaped concentric unit is given as Ai, and the calculation method Cal is designated as 'averaging'. In response to the 'averaging', as shown in FIG. 20, the processing control unit 31 outputs an average fault count $D_i$ for each concentric unit. The processing for the circumferential faults thereafter is similar to the processing described above.

Figure 21:
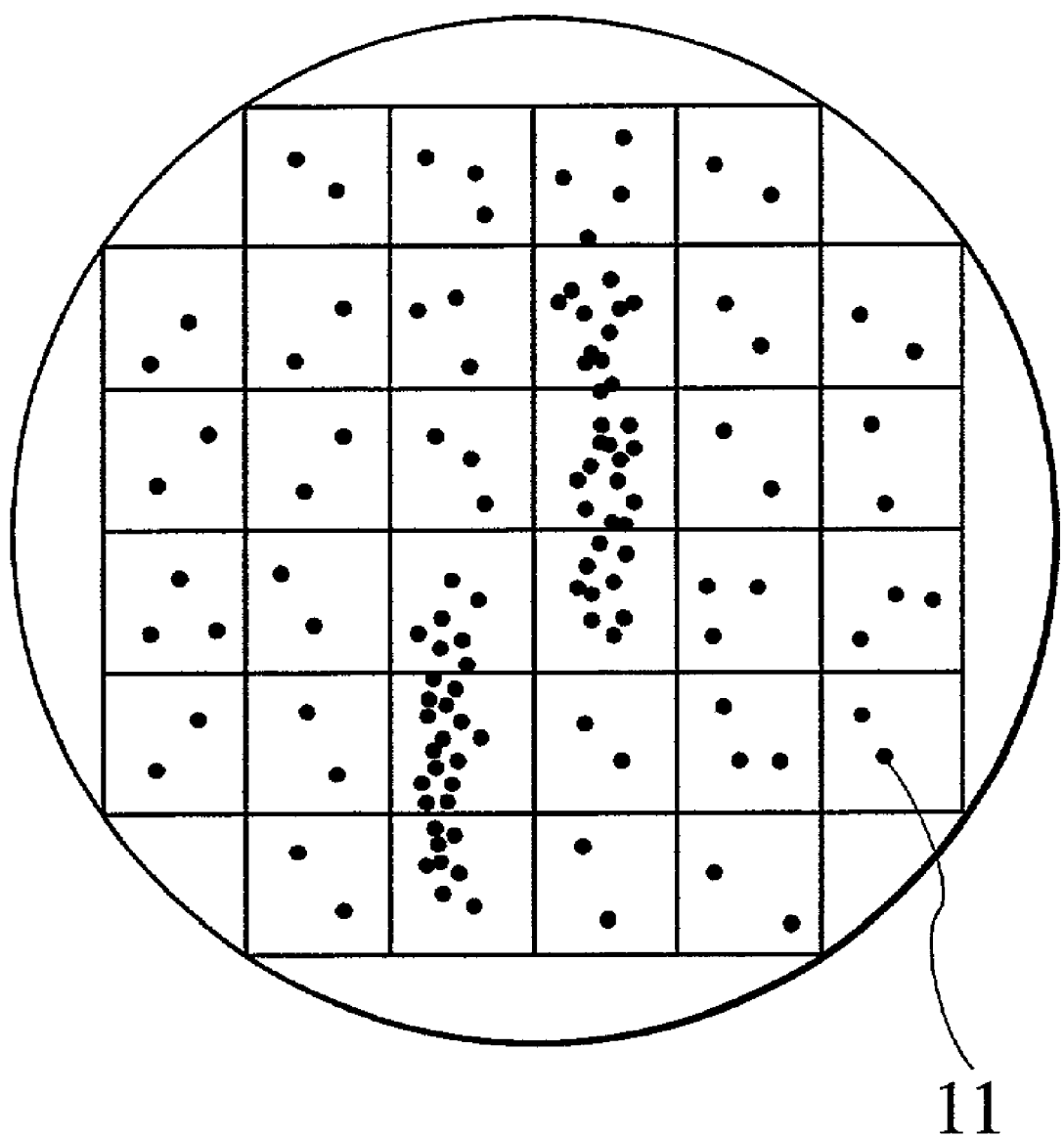
FIG. 21 is a fail bit distribution of a wafer following completion of a wafer process that forms DRAM according to third embodiment, where the wafer has an unknown fault pattern which has not been presupposed.

The newly found fault pattern shown in FIG. 21 is classified as an unknown pattern here at the stage. In the case of the newly found fault pattern, determination of whether symmetry exists within the surface is difficult. However, if some equipment-caused contributing factor exists, then intra-frame symmetry should also exist. The intra-frame symmetry is then located and A={A1, A2, . . . , An} is defined as the repeating unit thereof. Also, if the first characteristic factors calculation sub-routine is added, hereafter, auto classification as a registered fault pattern becomes possible.

Figure 22:
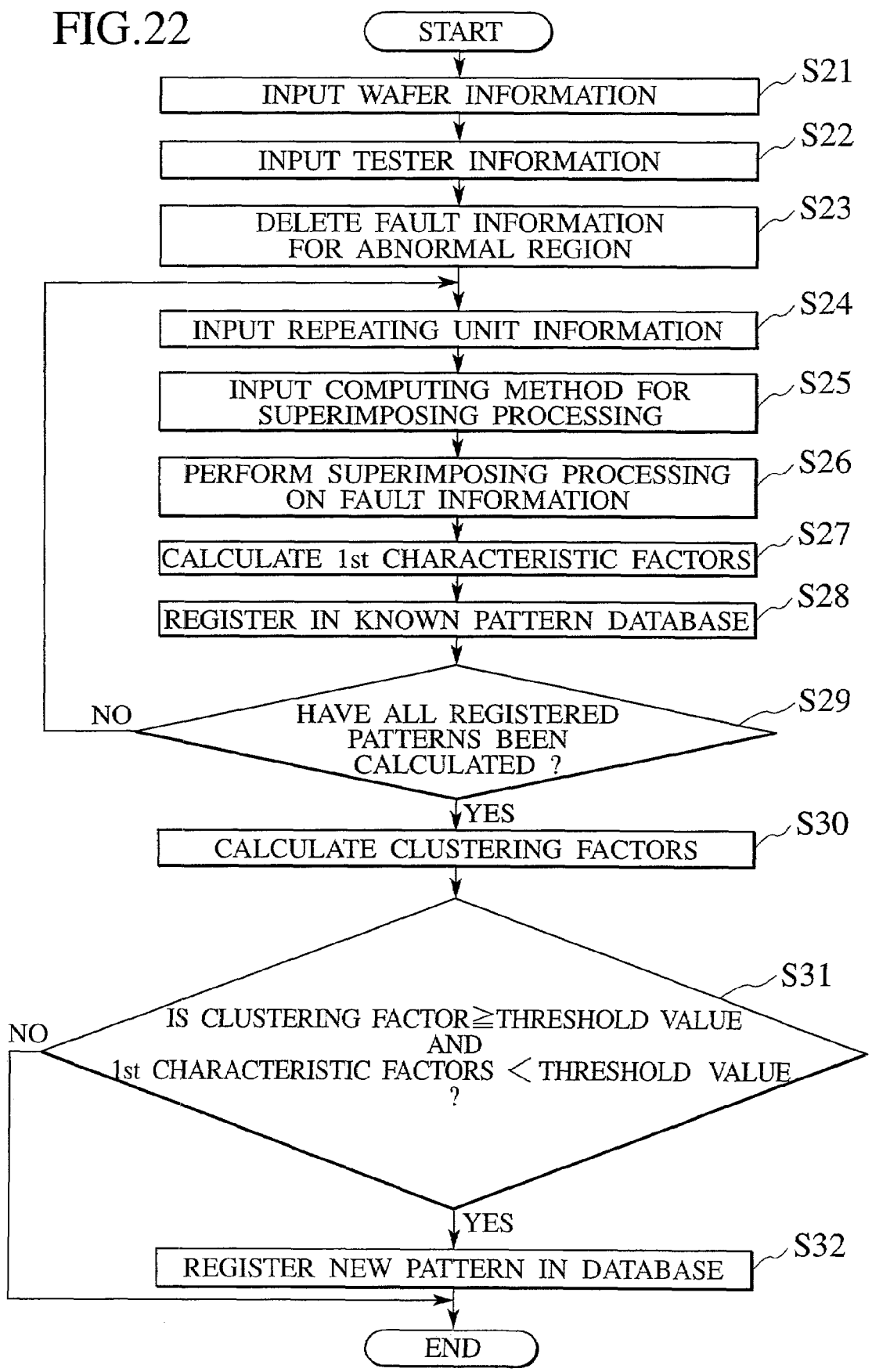
FIG. 22 is a flowchart illustrating a method of detecting unknown patterns according to the third embodiment.

A method of detecting faults according to the third embodiment will be explained using the example of wafer fault distribution shown in FIG. 21. On the wafer shown in FIG. 21, fault patterns having a concentration of vertically arranged faults 11 are highly visible. The fault patterns in FIG. 21 do not correspond to the fault patterns that are the object to be determined in the first and second embodiments. The unknown fault patterns are detected as an unknown pattern via the procedure shown in FIG. 22.

(I) Stage S21 imports the wafer information 7 into the processing control unit 31. Stage S22 imports the tester information 8 into the processing control unit 31. Stage S23 deletes the fault information of the isolated chip areas which have faults that may impede auto detection.

(II) Stage S24 inputs the repeating unit information. More specifically, the exposure unit information 9, the concentric unit information 22, and the user defined repeating unit information 29 are input to the processing control unit 31. Stage S25 inputs the calculation method for the superimposing process. More specifically, any of logical addition, logical multiplication, or averaging may be selected and used as the method of the superimposing repeating units. Then, in stage S26, in accordance with the input calculation method, superimposing is performed for every repeating unit.

(III) Stage S27 calculates the first characteristic factors illustrated in the first and second embodiments. More specifically, the profiling and parameterization of the fault counts for every exposure unit or concentric unit is carried out. The parameters are then standardized to fall within the range of 0 to 1, calculating the first characteristic factors. Stage S28 registers the determination results for known fault patterns into the first data storage unit 23. The known fault patterns denote the lithography-related or circumferential fault patterns. Stage S29 determines whether the operation (S24 to S28) has been performed for all pre-registered fault patterns, such as the exposure unit and concentric unit fault patterns. If there is a fault pattern for which the above-mentioned operation has not been performed ('No' in S29), it reverts back to S24, and the above-mentioned operation is performed for the fault pattern. If there are no fault patterns for which the above-mentioned processing has not been performed ('Yes' in S29), it proceeds to S30.

(IV) Stage S30 calculates clustering factors. More specifically, the technique for finding clustering factors is used. The clustering factors are second characteristic factors showing that there is polarization in the fault distribution within a wafer surface. A technique for finding the clustering factors is described forthwith.

To begin with, the fault count per chip area, and the frequency distribution thereof are found. The frequency distribution shows the fault count distribution within the wafer surface. The frequency distribution is then approximated by superimposing a Poisson distribution and a negative binomial distribution. Namely, the fault count distribution within the wafer surface is represented by a linear combination of a Poisson distribution and a negative binomial distribution. The Poisson distribution shows that the fault count distribution is spatially random. The negative binomial distribution shows that polarization occurs in the fault count distribution. Large components in the negative binomial distribution show greater polarization occurring in the fault count distribution.

The Poisson distribution weight (Wp) and the negative binomial distribution weight (Wnb) are determined, and the negative binomial distribution weight (Wnb) is defined as the clustering factor. Since Wp +Wnb=100%, it shows that the larger Wnb is, the greater the spatial polarization is. In the case of the wafer shown in FIG. 21, Wnb is 14%, which is considered a large value.

(V) Stage S31 decides whether there exists an unknown pattern which has not been presupposed. In other words, what mode of fault cannot be determined, but the existence of some unknown pattern can be detected. The detection of an unknown pattern is performed using the value of Wnb and first characteristic factors relating to the registered fault patterns. The registered fault patterns denote the lithography-related or circumferential fault patterns that have already been registered. More specifically, when Wnb is higher than a predetermined threshold value, and the first characteristic factors of a registered fault pattern are lower than a predetermined threshold value, the existence of an unknown pattern is detected. When the existence of an unknown pattern is detected ('Yes' in S31), the detected unknown pattern is registered in the second data storage unit 24 (S32).

FIG. 23 shows the calculation results of the clustering factor (Wnb), the first characteristic factors S for the lithography-related fault, and the first characteristic factor P for the circumferential faults. The first characteristic factor S indicates the larger of the scan direction or slit direction first characteristic factors. As shown in FIG. 23, the wafer with the wafer ID of 'A' has a vertical fault pattern. For the wafer A, since both first characteristic factors S and P are small, and Wnb is large, it is determined that the vertical fault pattern is an unknown pattern. The wafer with the wafer ID of 'B' has random faults. For the wafer 'B', since the first characteristic factors S and P, and Wnb are all small, it is determined that the wafer 'B' has a random distribution. The wafers with the wafer ID of 'C' and 'D' have the registered lithography-related and circumferential fault patterns, respectively. For both wafer 'C' and wafer 'D', Wnb is large for both, and the respective first characteristic factors (S, P) thereof are also large. Accordingly, the wafer 'C' and wafer 'D' are respectively determined to have already registered fault patterns.

The first to third embodiments emphasize the fault pattern symmetry by the superimposing processing. The emphasizing fault patterns in which the symmetry does not exist would be useless. For example, in the case where an irregularly-shaped scratch develops upon the wafer due to human error, the emphasizing processing by the superimposing would be useless. Accordingly, the data used in the first characteristic factor calculation is the fault count information as it is. Nevertheless, in a case where a scratch develops in a certain direction due to the mechanical irregularities, the superimposing processing which emphasizes that certain direction can be used. For example, scratches that develop due to irregularities during chemical mechanical polishing (CMP) can also have symmetry corresponding to features of the above-mentioned processing. Even in case of the scratches, the third embodiment can be considered effective. Furthermore, in cases where two or more modes of faults simultaneously exist, an overlapping region showing such symmetry may also be set.

Moreover, there is a manufacturing equipment that processes the wafer surface by segmenting it into fixed regions. The exposure equipment is one such equipment. However, besides the exposure equipment, a laser annealing equipment may alternatively be used. Herein, processing units are decided by the shape of the laser beam and the movement of the x-y stage. For example, in the case where laser annealing is performed in the multiple chip area units, the faults caused by the laser annealing may be appear in the multiple chip area periods corresponding to the laser irradiation unit. In such a case, the superimposing processing should be carried out using the repeating units of the multiple chip areas. There are also cases where the wafer surface scanning is done using a point-like laser beam. In the case of the point-like laser beam, the region where the scanning hits in the forward (or reverse) direction can be considered to be the repeating unit. Moreover, there are also cases where a linear beam scans in one direction. In the case of the scans in one direction, one complete scan region of the linear beam should be used as the repeating unit. In this manner, by making the intra-wafer processing unit the repeating unit, it is possible for the device-caused faults to be emphasized.

As described in the preceding, faults in the semiconductor integrated circuits often have some sort of symmetry or periodicity. Accordingly, the first to third embodiments can be considered effective. By using the method for detection of the faults illustrated in the third embodiment, it is possible for an unknown pattern to be auto detected, and it is possible to register unknown fault patterns with ease.

(Fourth Embodiment)

In the fourth embodiment, equipment for and a method of calculating the degree of influence of each fault pattern on yield using the fault detection results will be explained. The degree of influence on yield can be calculated by comparing the auto classified fault pattern with the yield information.

Figure 24:
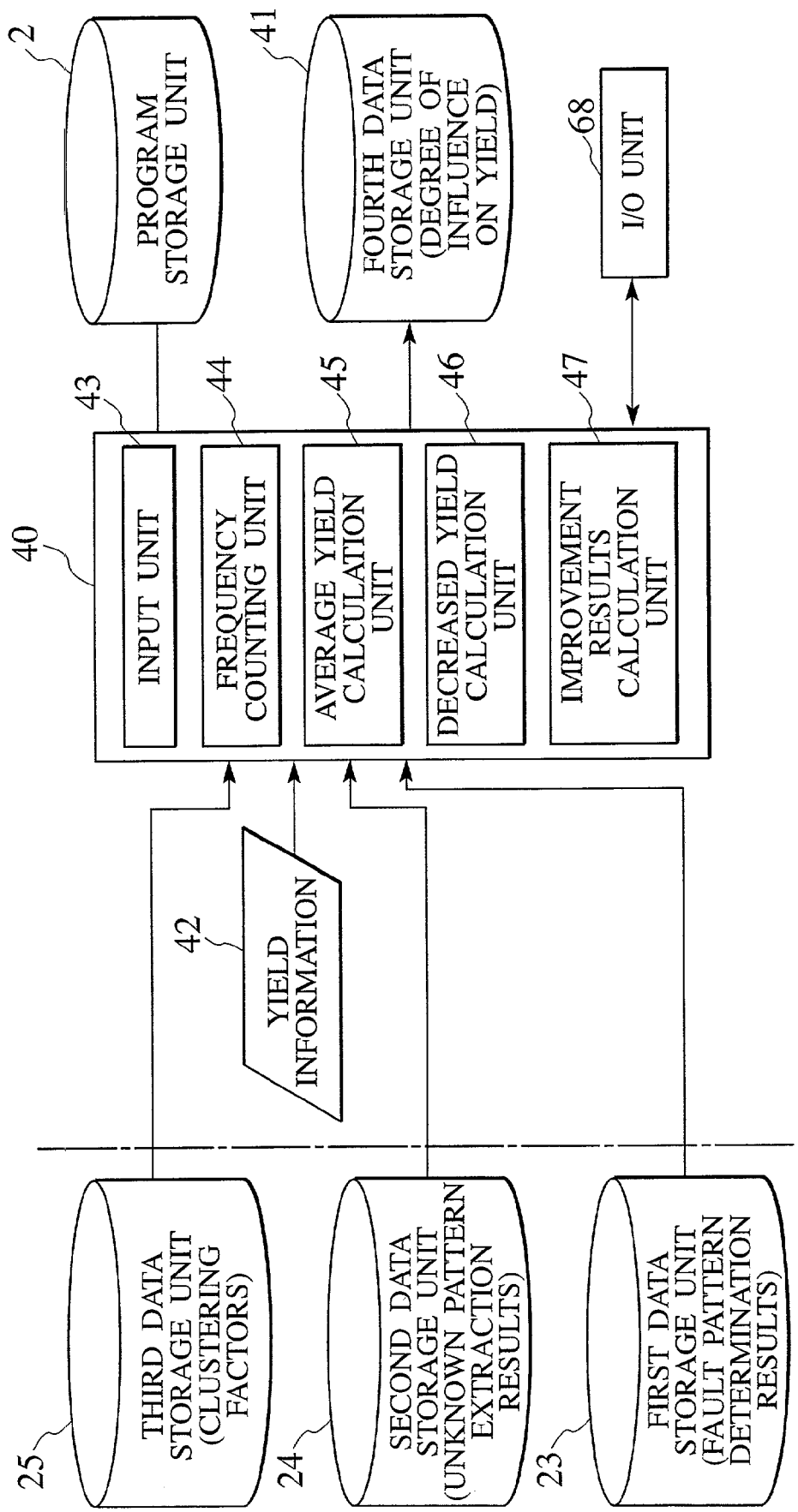
FIG. 24 is a block diagram showing an equipment for calculating the degree of influence on fault pattern yield according to the fourth embodiment.

As shown in FIG. 24, the equipment according to the fourth embodiment is connected to the equipment shown in FIG. 16 via the first to third data storage units (23 to 25). The equipment according to the fourth embodiment includes a processing control unit 40, a program storage unit 2, a data storage unit 41, and an I/O unit 68. The processing control unit 40 has function blocks for calculating the degree of influence on yield of a fault pattern recorded in the first database 23. More specifically, the processing control unit 40 includes an input unit 43, a frequency counting unit 44, an average yield calculation unit 45, a decreased yield calculation unit 46, and an improvement results calculation unit 47.

The input unit 43 inputs the fault pattern classification, clustering factor, and unknown pattern extraction result from the first to third data storage units (23 to 25) into the processing control unit 40. In addition, the input unit 43 inputs the yield-related information 42 into the processing control unit 40. The frequency counting unit 44 counts the fault pattern development frequency, the development frequency of a wafer with no distribution polarization, and the development frequency of a wafer where an unknown pattern exists. The average yield calculation unit 45 calculates the average yield from the detection result of the faults and the yield information. The decreased yield calculation unit 46 calculates the reduced amount of yield due to the fact that a registered fault pattern or an unknown fault pattern exists. The improvement results calculation unit 47 calculates the results in the yield improvement due to the resolution of faults, polarized fault distribution, or unknown pattern. The data related to the calculated yield improvement results are registered in the fourth data storage unit 41.

Figure 25:
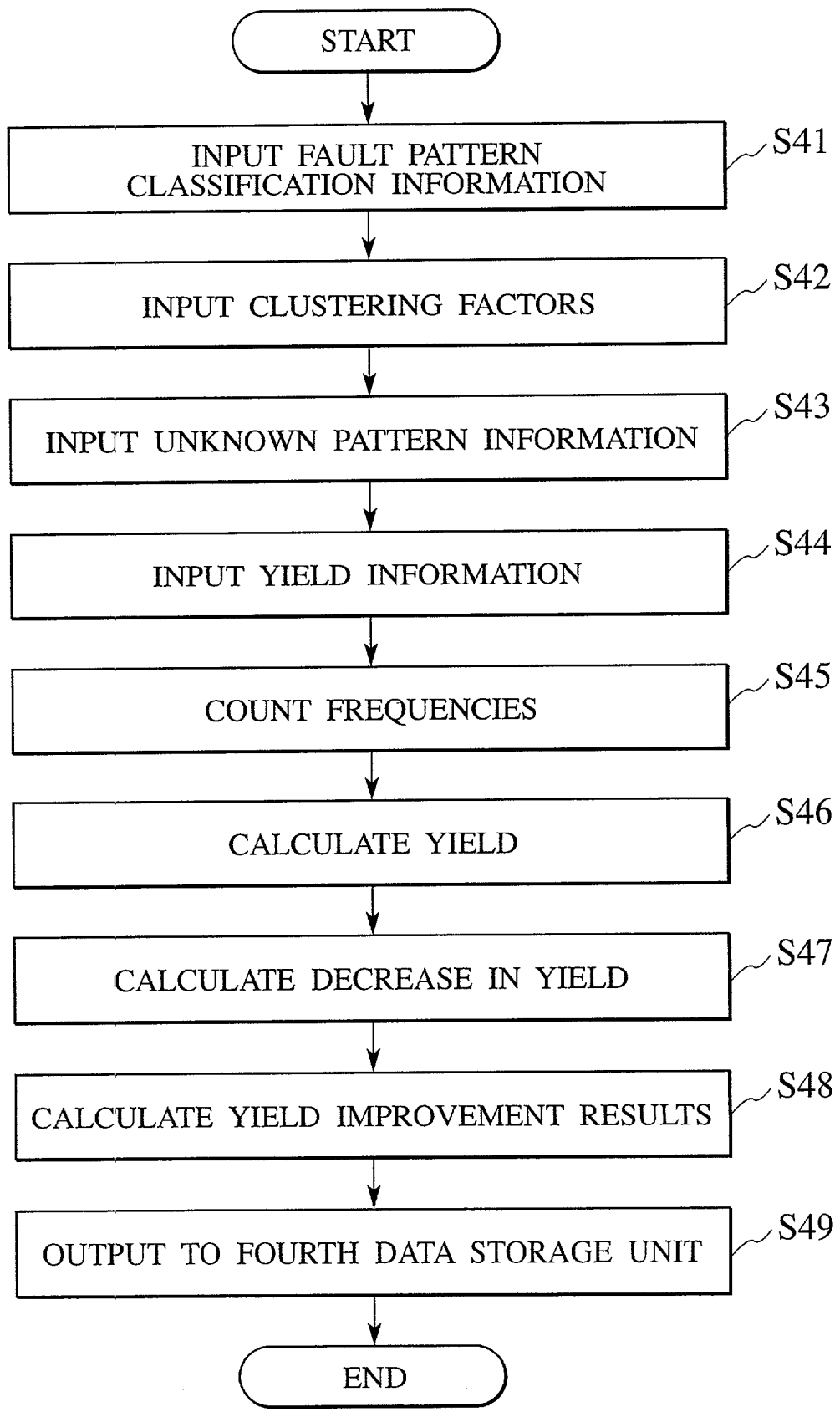
FIG. 25 is a flowchart illustrating a method of calculating the degree of influence on fault pattern yield using the equipment of FIG. 24.

A method of calculating the degree of influence on the yield of each fault pattern using the equipment shown in FIG. 24 will be explained with reference to FIG. 25. It is noted that the N modes of fault patterns, pattern 1 through pattern N, are stored in the first data storage unit 23.

(I) To begin with, stage S41 inputs the classification information for the registered N modes of fault patterns from the first data storage unit 23. Stage S42 inputs information related to clustering factors for each wafer from the third data storage unit 25. Then, stage S43 inputs information related to a wafer on which an unknown pattern has been detected from the second data storage unit 24. Stage S44 inputs information related to the yield of each wafer.

(II) Stage S45 counts the development frequency of each registered fault pattern, the development frequency of a wafer with no distribution polarization, and the development frequency of a wafer where an unknown pattern exists. Stage S46 calculates the average yield of a wafer where a registered fault pattern has been generated, the average yield of a wafer with no distribution polarization, and the average yield of a wafer where an unknown pattern exists.

More specifically, the development frequency of the pattern i is counted while referencing the first data storage unit 23. The average yield Yi for all wafers, where it is determined the pattern i exists, is calculated while referencing the yield information 42. In addition, the development frequency fR of a wafer with no fault distribution polarization is counted. The average yield YR for that wafer is calculated while referencing the third data storage unit 25. While referencing the second data storage unit 24, the development frequency fX of a wafer where an unknown pattern exists is counted, and the average yield YX for that wafer is calculated.

(III) Stage S47 calculates decrease in the yield amount ΔYi due to the pattern i existing by using expression (11).

$$\Delta Yi = YR - Yi \quad (11)$$

In the same manner, decrease in the yield amount ΔYX due to an unknown pattern existing is calculated using expression (12).

$$\Delta YX = YR - YX \quad (12)$$

(IV) Stage S48 calculates the yield improvement results ΔEi by using expression (13). ΔEi is expected for all wafers if there is no pattern i.

$$\Delta Ei = (fi/\text{fall})\Delta Yi \quad (13)$$

In the same manner, the yield improvement results ΔEX are calculated using expression (14). ΔEX is expected for all wafers if there is no unknown patterns.

$$\Delta EX = (fX/\text{fall})\Delta YX \quad (14)$$

The total wafer count is represented by expression (15).

$$\text{fall} = fR + fx + \sum_{i=1}^{N} fi \quad (15)$$

(V) Finally, Stage S49 writes each counting result in the fourth data storage unit 41. The user is then able to easily spot the influence of a fault pattern on the yield by referencing the fourth data storage unit 41. Since the lithography-related faults actually have a large development frequency and the decrease in the yield is also large, the yield improvement result will certainly be high.

As described in the above, according to the fourth embodiment, the user is able to easily spot the influence of a fault pattern on the yield.

(Fifth Embodiment)

In the fifth embodiment, equipment for and a method of specifying the cause of development of each fault pattern using the fault detection results will be explained. Each fault pattern development cause can be specified by comparing the auto classified fault pattern with the equipment history information and the quality control data information.

Figure 26:
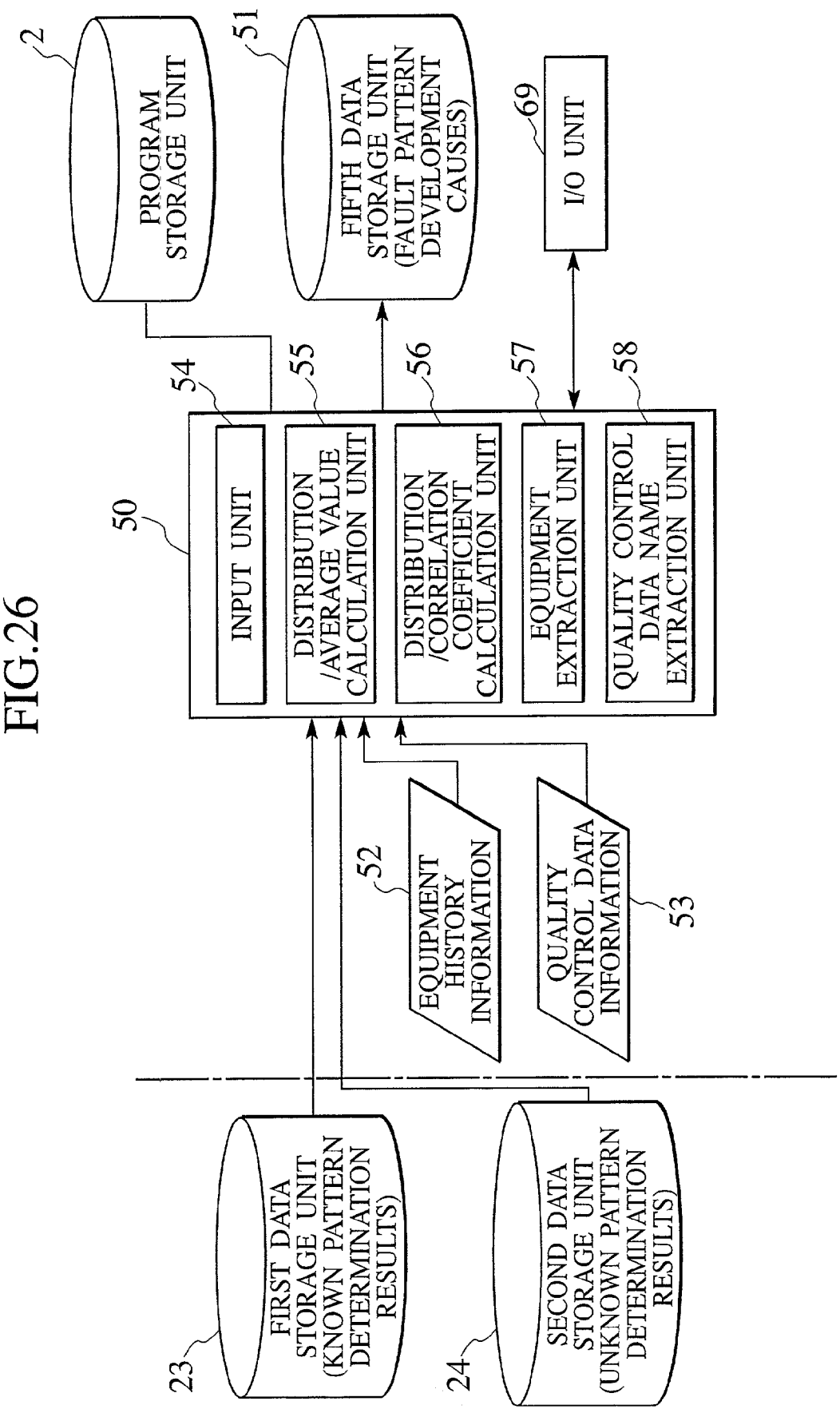
FIG. 26 is a block diagram showing an equipment for specifying causes of fault pattern development according to the fifth embodiment.

As shown in FIG. 26, the equipment according to the fifth embodiment is connected to the equipment shown in FIG. 16 via the first and second data storage unit 23, 24. The equipment according to the fifth embodiment includes a processing control unit 50, a program storage unit 2, fifth data storage unit 51, and an I/O unit 69. The processing control unit 50 specifies the fault pattern development cause of a fault pattern registered in the first database 23. More specifically, the processing control unit 50 includes an input unit 54, a distribution/average value calculating unit 55, a distribution/correlation coefficient calculation unit 56, an equipment extraction unit 57, and a quality control data name extraction unit 58.

The input unit 54 inputs information on the fault pattern classification and the results of unknown pattern extraction into the processing control unit 50. In addition, the input unit 54 inputs the equipment history related information 52 and the quality control data related information 53 into the processing control unit 50. The distribution/average value calculation unit 55 forms frequency distributions of the first characteristic factors for every equipment in the manufacturing processes, and calculates the average value of the first characteristic factors. The distribution/correlation coefficient calculation unit 56 compares the first characteristic factors with the quality control data and calculates a correlation coefficient between them. The equipment extraction unit 57 extracts the equipment for which the first characteristic factor frequency exceeds a predetermined threshold value. The quality control data name extraction unit 58 extracts the quality control data names for which the correlation coefficient with the first characteristic factors exceeds a predetermined threshold value. The extracted equipment and the quality control data names are then registered in the fifth data storage unit 51.

Figure 27:
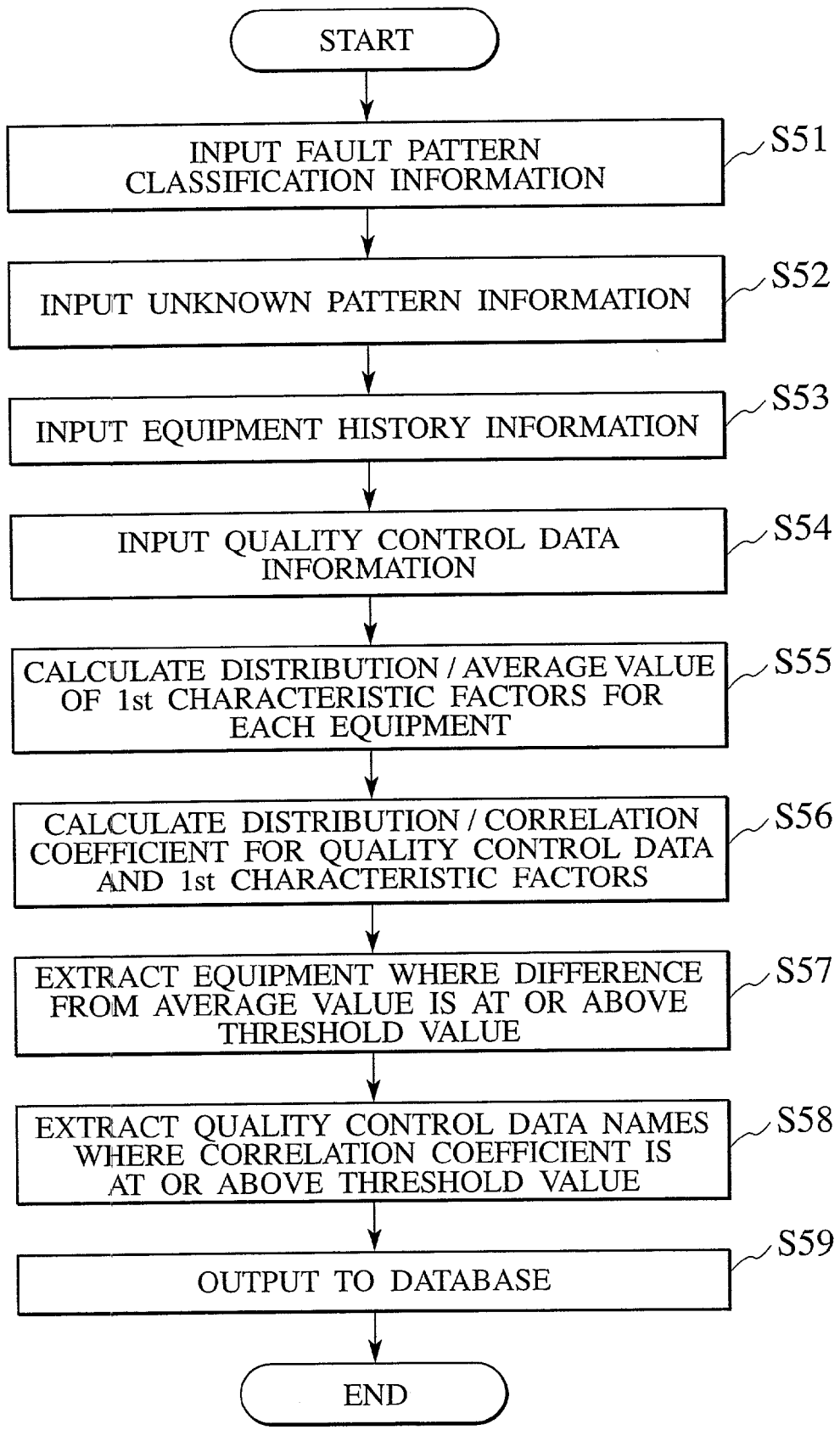
FIG. 27 is a flowchart illustrating a method of specifying causes of fault pattern development using the equipment of FIG. 26.

A method of specifying fault pattern development causes using the equipment shown in FIG. 26 will be explained with reference to FIG. 27.

(I) Stage S51 inputs the classification information for the registered N modes of fault patterns from the first data storage unit 23. Then, stage S52 inputs information related to a wafer on which an unknown pattern has been detected from the second data storage unit 24. Stage S53 inputs the equipment history related information 52 for each wafer. Stage S54 inputs the quality control related information 53 for each wafer.

(II) Stage S55 forms the first characteristic factors frequency distribution shown in FIG. 28 for every equipment in each manufacturing process. The first characteristic factor frequency distribution is formed by comparing the first characteristic factors for each wafer with the equipment history information 52. The first characteristic factors for each wafer are registered in the first data storage unit 23. Then, from the first characteristic factor frequency distribution, the average value of the first characteristic factors for all equipment is calculated. The calculated average value is registered in the fifth data storage unit 51.

(III) Stage S56 forms distribution maps as shown in FIG. 29 for all equipment in each manufacturing process. The distribution maps are formed by comparing the quality control data with the first characteristic factors. The quality control data is taken from the quality control data information 53. The correlation coefficient of each quality control data and the first characteristic factors is calculated. The calculated correlation coefficient is then registered in the fifth data storage unit 51.

(IV) Stage S57 extracts equipment for which the difference from the average first characteristic factors of the equipments exceeds a preset threshold value. The name of the extracted equipment and the manufacturing processes using the extracted equipment are then registered in the fifth data storage unit 51.

(V) Stage S58 extracts equipment for which the correlation coefficient of each quality control data and the first characteristic factor exceeds a preset threshold value. The quality control data name of the extracted equipment is then registered in the fifth data storage unit 51. In effect, the fact that the first characteristic factor average value is high in exposure equipments used in a predetermined exposure process has been detected. In addition, it is clear that there is a strong correlation with the quality control data connected to that exposure process, which can shed light upon the cause of faults.

As described above, according to the fifth embodiment, causes of the fault pattern development can be efficiently specified.

As described in the preceding, the faults of semiconductor integrated circuits can be emphasized by superimposing the repeating units representing symmetry or periodicity thereof. By finding the first characteristic factors from the emphasized faults, highly sensitive detection of faults is possible. In addition, in the case where polarization of faults exists within the wafer surface, the clustering factor representing the degree of fault polarization can be compared with the first characteristic factors of the registered fault patterns. The existence of unknown patterns that have not been presupposed can be auto detected.

(Sixth Embodiment)

An equipment for detecting faults according to the sixth embodiment of the present invention finds vectors each having components of a plurality of first characteristic factors, and performs identification of a fault pattern in the vector space configured by these vectors. The equipment of the sixth embodiment, in particular, determines the intrasurface distribution.

Figure 30A:
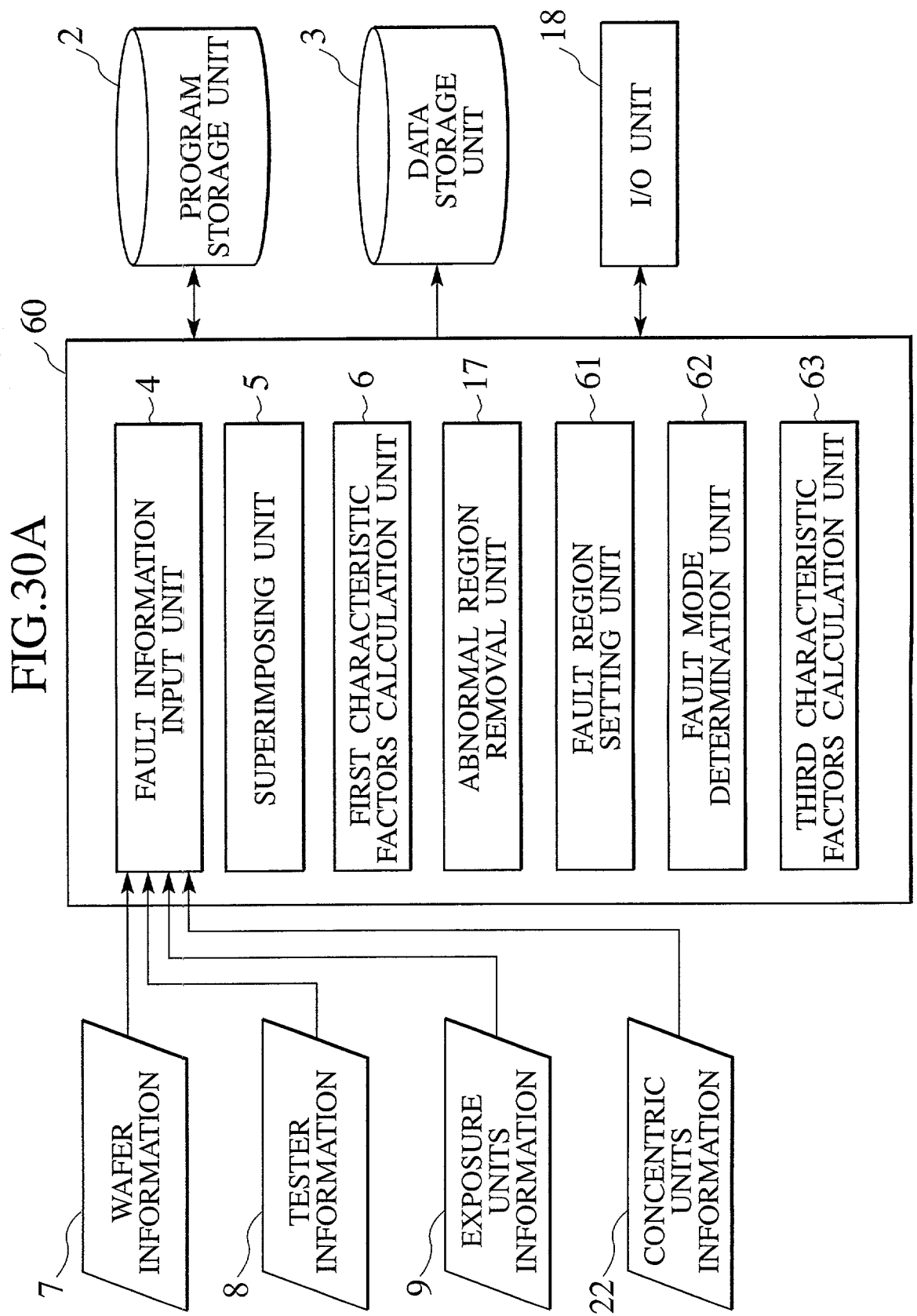
FIG. 30A is a block diagram showing a fault pattern detection equipment according to the sixth embodiment.

As shown in FIG. 30A, the equipment for detecting faults according to the sixth embodiment has a process control unit 60, a program storage unit 2, a data storage unit 3, and an I/O unit 18. The process control unit 60 has a fault information input unit 4, a superimposing unit 5, a first characteristic factors calculation unit 6, an abnormal region removal unit 17, a fault region setting unit 61, a fault mode determination unit 62, and a third characteristic factors calculation unit 63. In comparison with the equipment shown in FIG. 10, the process control unit 1 differs in the fact that it has the fault region setting unit 61, the fault mode determination unit 62, and the third characteristic factors calculation unit 63.

The fault region setting unit 61 forms a vector space in accordance with the vectors having a plurality of first characteristic factors as components. Hereafter, vector space is referred to as "characteristic factors space". The fault region setting unit 61 then sets a fault region within the characteristic factors space corresponding to one of the fault modes. The plurality of first characteristic factors has first characteristic factors showing various topologies of fault modes and first characteristic factors showing location within the wafer surface. For example, the plurality of first characteristic factors may have first characteristic factors of lithography-related or circumferential faults.

The fault mode determination unit 62 verifies the fault region with the vector, and determines the fault mode.

Figure 30B:
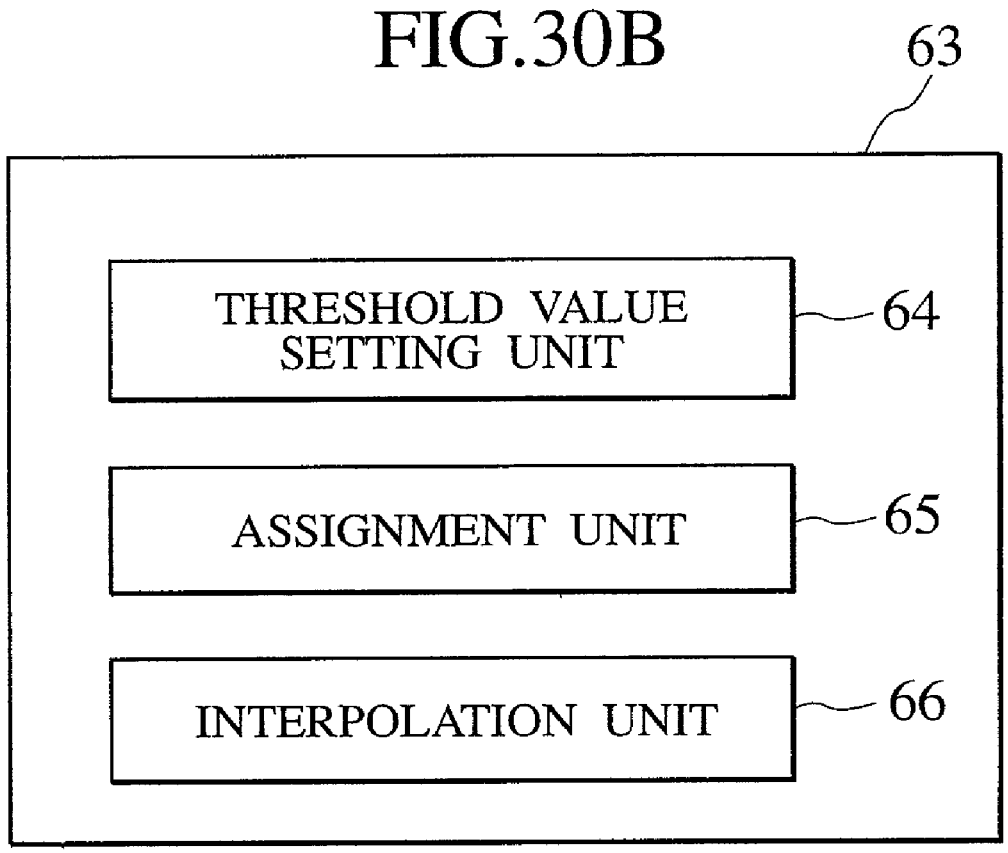
FIG. 30B is a block diagram showing the third characteristic factors calculation unit in FIG. 30A.

The third characteristic factors calculation unit 63 calculates the third characteristic factors having scalar amounts showing the degree of fault mode. As shown in FIG. 30B, the third characteristic factors calculation unit 63 includes a threshold value setting unit 64, an assignment unit 65, and an interpolation unit 66. The threshold value setting unit 64 sets the upper limit region, the lower limit region, and the threshold value region of the degree of fault mode within the vector space. The assignment unit 65 arranges the third characteristic factors in the upper limit region, the lower limit region, and the threshold value region. The interpolation unit 66 interpolates among the upper limit region, lower limit region, and threshold value region. In addition, interpolation unit 66 performs linear interpolation relating to the distance within the characteristic factors space.

Figure 31:
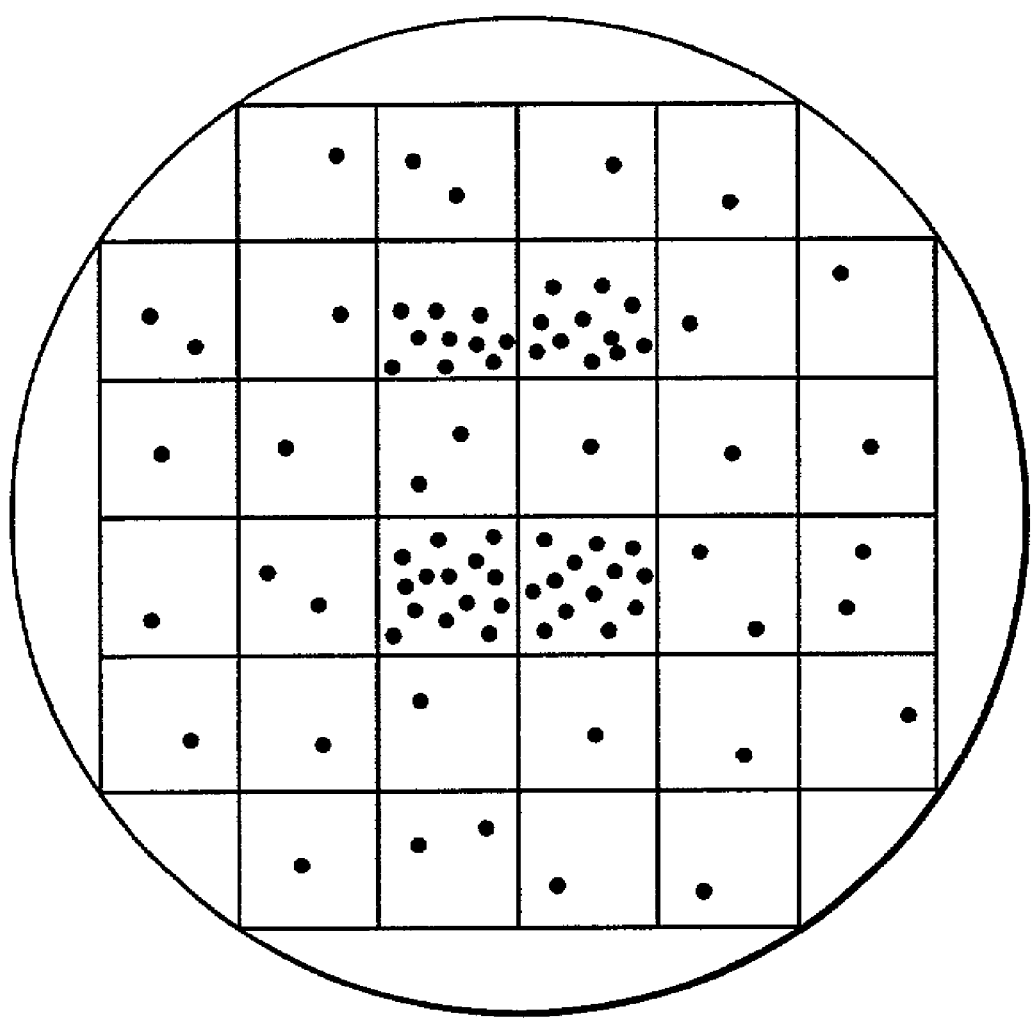
FIG. 31 shows is a planar view showing the distribution of fault bits on a post-wafer processing DRAM, which shows the condition where many lithography-related fault bits are developing at the center of the wafer.
Figure 32:
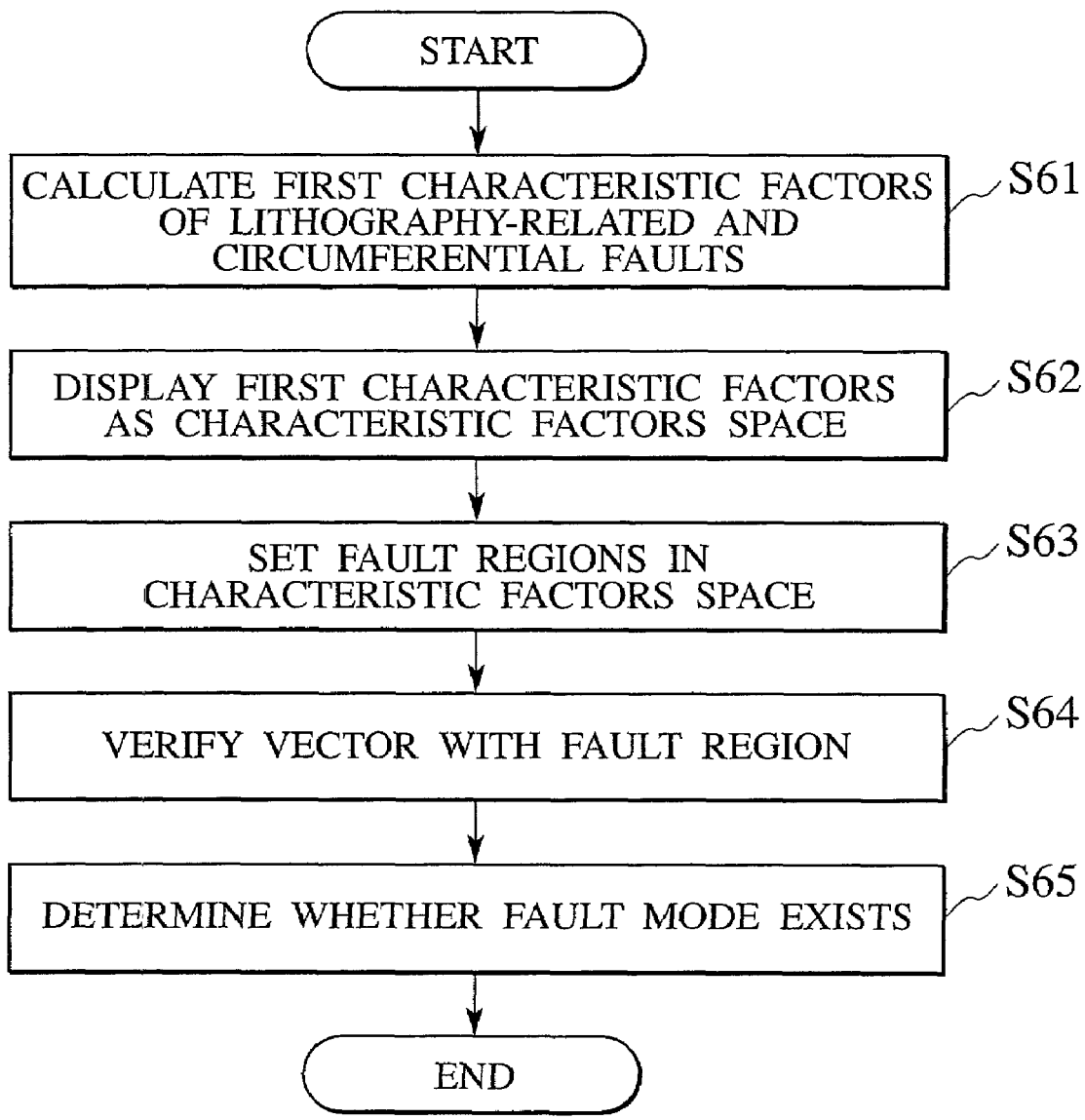
FIG. 32 is a flowchart showing a fault pattern detection method according to the sixth embodiment.

FIG. 31 shows the results of testing of each bit on each post-wafer processing DRAM chip. The wafer has a lithography-related fault pattern. Such fault pattern is localized in the center portion of the wafer. In order to specify the manufacturing equipment at fault, it is necessary to distinguish between a fault developing on the whole wafer surface, and a fault developing polarized within the wafer surface. Therefore, a method for simultaneously performing fault pattern detection and determination of the distribution within such surface is described forthwith while referencing FIG. 32.

(A) In stage S61, the lithography-related first characteristic factors are found with the method shown in the first embodiment. The lithography-related first characteristic factors have a scan direction characteristic factor (Sx) and a slit direction characteristic factor (Sy). The two first characteristic factors represent the two-dimensional vector (Sx, Sy).

(B) In addition, in stage S61, a circumferential first characteristic factor Pr is found using the method shown in the second embodiment. The average number of faults in a region less than r/2 is given as m1, and the average fault count of a region equal to or greater than r/2 is given as m2. The first characteristic factor Pr is defined with equation (16).

$$Pr = m2/(m1+m2) \qquad (16)$$

Pr becomes 0 as the number of failure bits polarizes towards the center of the wafer; conversely, Pr becomes 1 as the number of failure bits polarizes towards the outer circumference. When failure bits exist evenly throughout the entire surface of the wafer, Pr is 0.5.

FIG. 33 shows the results from finding the first characteristic factors (Sx, Sy, and Pr) regarding wafers where several fault patterns exist. It is understood from the first characteristic factors (Sx, Sy) that lithography-related faults have developed. Moreover, it is understood from first characteristic factor Pr that the lithography-related faults exist at the center of the wafer, throughout the entire wafer, and at the outer circumference of the wafer, respectively.

Figure 34:
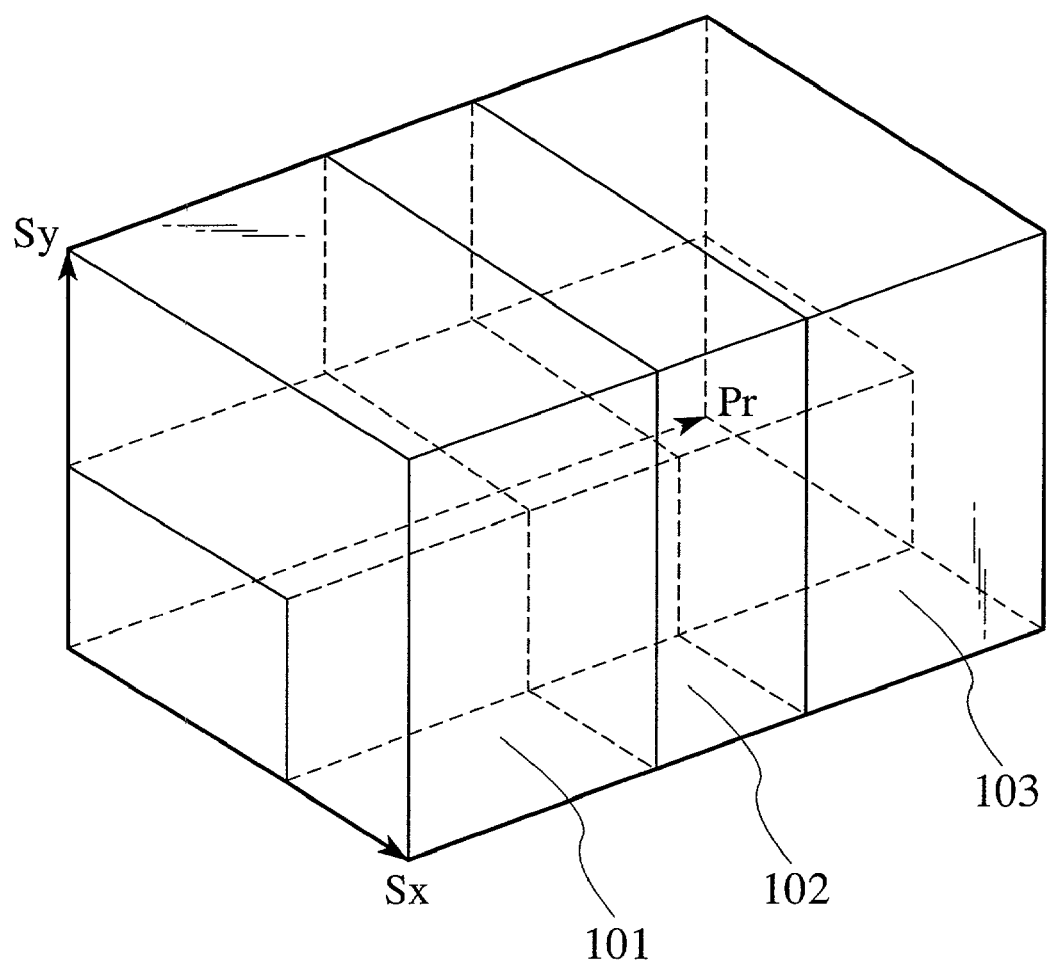
FIG. 34 is a perspective view showing a fault region corresponding with a characteristic factors space having the first characteristic factors (Sx, Sy, Pr) and each of the fault modes.

(C) In stage 62, the vector having the first characteristic factors (Sx, Sy, Pr) are represented as a characteristic factors space. In stage S63, as shown in FIG. 34, the respective threshold values for Sx, Sy, and Pr are set. Each fault region separated by the threshold values represents each fault mode of fault pattern. For example, each fault region exhibits central-wafer lithography-related faults 101, all-over lithography-related faults 102, and circumferential lithography-related faults 103, respectively.

(D) In stage S64, the vector is verified with the fault region. In stage S65, the fault mode is determined.

Fault distribution in the characteristic factors space is an effective when determination condition is complicated. In the case where a fault pattern exists within only a portion of the wafer surface, the detection sensitivity of the first characteristic factors is dulled. When lithography-related faults exist at only the center of the wafer, the first characteristic factors have a value which is smaller than that in the case where they exits throughout the entire surface of the wafer. It is the same for the case where lithography-related faults exist at only the circumference of the wafer. Therefore, it is possible to reduce mis-determinations by modifying the threshold values for the first characteristic factors (Sx, Sy) based on the first characteristic factor Pr. More specifically, the edges of the rectangular parallelepiped near Pr=0 and 1 are shortened, forming the fault region shown in FIG. 35. The fault region is verified with the vector to determine the fault mode.

It is noted that in order to determine the intra-surface distribution, the superimposed shot region may be limited to the region for which determination of the intra-surface distribution is wanted. In the case of the wafer of FIG. 31, superimposition in the respective shot units may be performed within the region inside of the r/2 ring and outside of the r/2 ring, respectively. The superimposition in the respective shot units is effective in the case where the first characteristic factors are linear, or in the case where the superimposition principle is effected.

However, in the case where the first characteristic factors are non-linear, the shading of fault pattern and the magnitude of the first characteristic factors do not always match. In the case where the first characteristic factors (Sx, Sy) are non-linear, and there is shading in the fault pattern, the first characteristic factors (Sx, Sy) tend to become somewhat smaller. The first characteristic factors (Sx, Sy) lack quantitativity so that the first characteristic factors (Sx, Sy) are not suitable for determining the intra-surface distribution. The first characteristic factors are not always limited to being linear. Accordingly, a method where the characteristic factors are specially set up so as to determine the intra-surface distribution, and determination is made within the characteristic factors space is effective.

As described above, according to the sixth embodiment, a lithography-related fault pattern and the intra-surface distribution thereof can be found with high accuracy.

(Modification 1 of the Sixth Embodiment)

With a modification 1 of the sixth embodiment, determination of fault patterns similar to each other in the characteristic factors space is made so as to attain fewer mis-determinations.

Figure 36A:
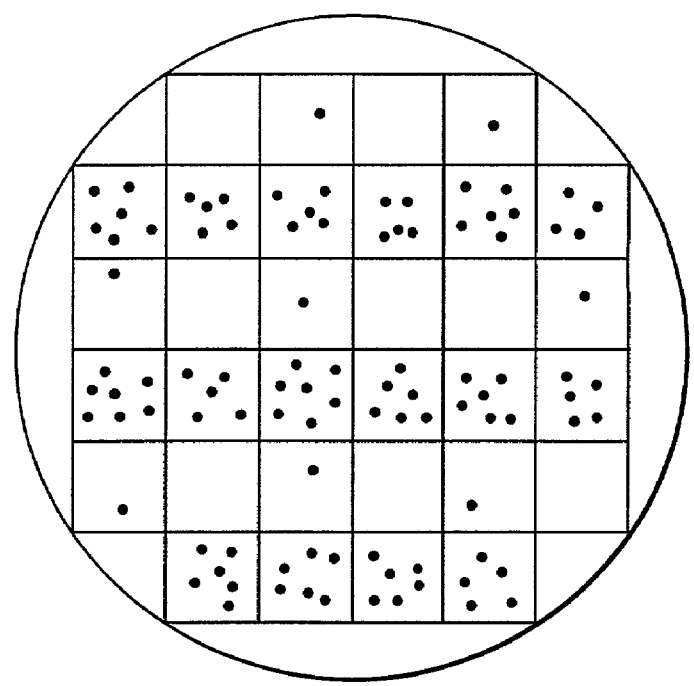
FIG. 36A is a planar view showing a wafer having a lithography-related fault pattern.
Figure 36B:
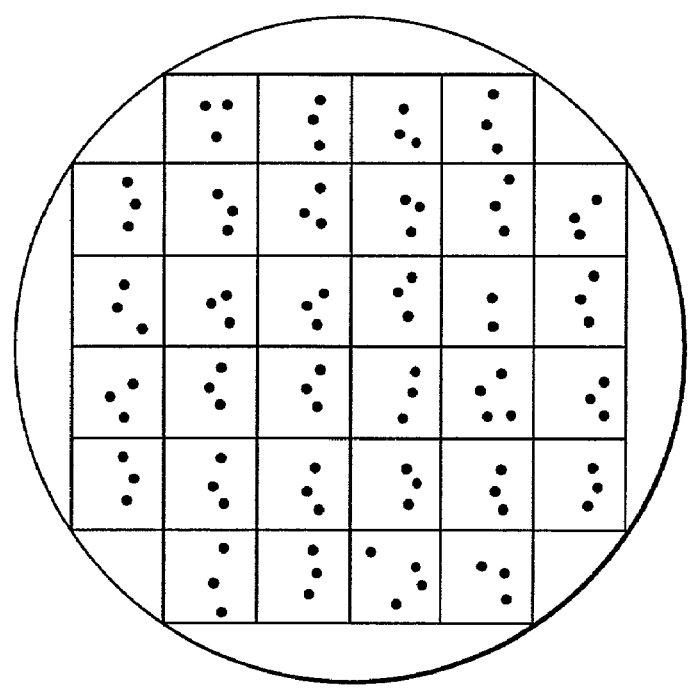
FIG. 36B is a planar view showing a wafer having chip properties-related faults.

The wafer of FIG. 36A has faults (lithography-related faults) that repeats every exposure unit. On the other hand, the wafer of FIG. 36B has faults (chip properties-related faults) that repeats every chip. The wafer of FIG. 36A can be considered as having fault causes stemming from the exposure equipment. However, the wafer of FIG. 36B can be considered as having fault causes different from those of the wafer in FIG. 36A. Nonetheless, in the results of superimposing in an exposure unit the fault information of the wafer in FIG. 36B, the first characteristic factors (Sx, Sy) for lithography-related faults become a large value. Accordingly, the wafer of FIG. 36B is wrongly determined as having a lithography-related fault pattern. Therefore, in conformity with the following procedure, the first characteristic factors according to faults stemming from chip properties, are newly defined.

Figure 37:
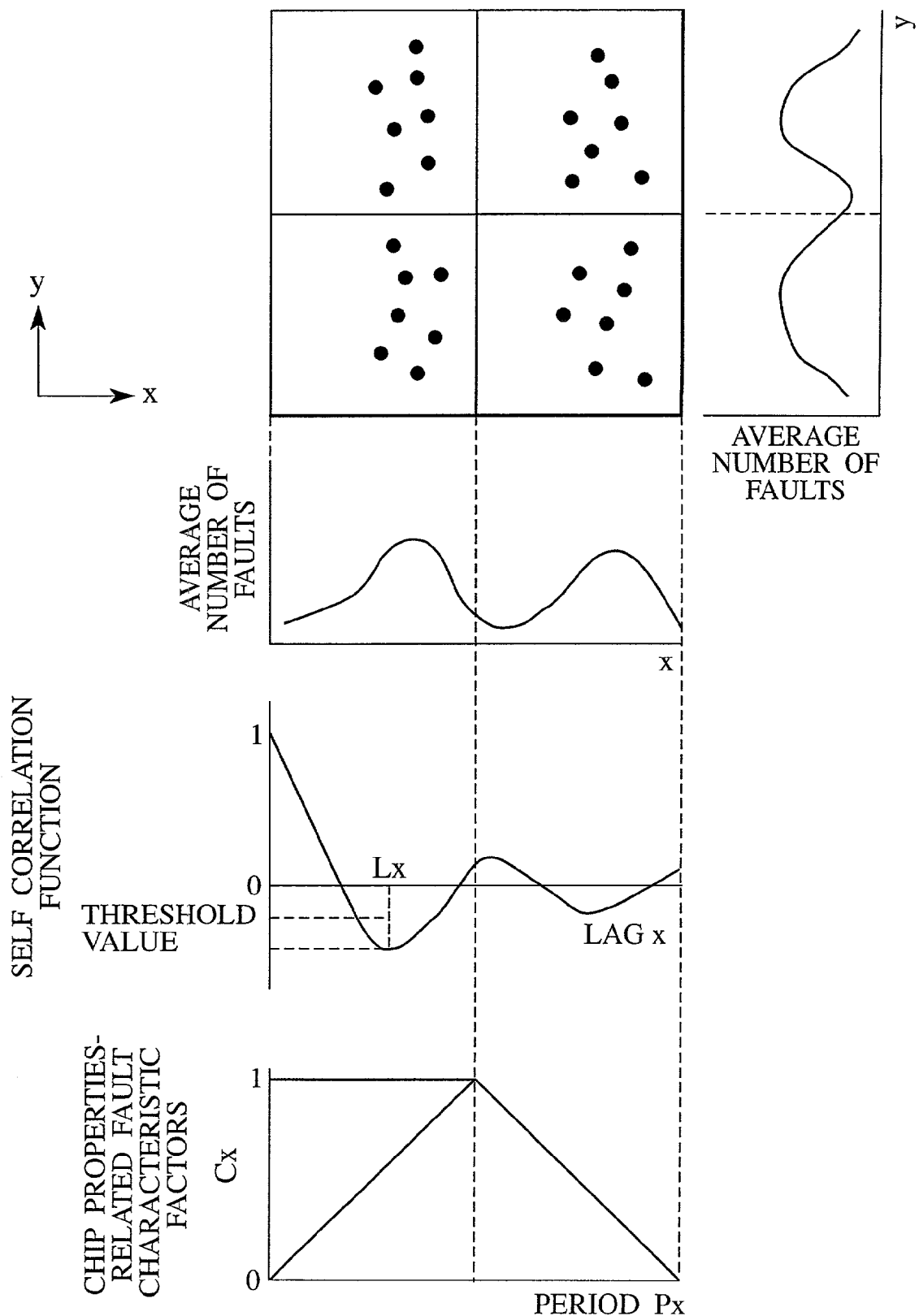
FIG. 37 shows a method of defining the first characteristic factors according to chip properties-related faults.

(I) Turning back to FIG. 2, fault information is input (S01), and fault information of isolated chips is deleted. The fault information is superimposed every exposure unit (S03), and an average fault count distribution such as that shown in FIG. 37 is calculated. Then respective 1-D, profiles projected in the scan direction and slit direction are produced.

Using the auto correlation function of each 1-D profile, the chip periodicity of the 1-D profile is found. The lag width to the first local minimal point of the auto correlation function, corresponds to the half cycle (antiphase) of the auto correlation function. For example, the auto correlation function of the 1-D profile in the scan direction (x direction) is considered. When the lag width of the first local minimal point is Lx, the period Px in the x direction becomes 2×Lx. The first characteristic factor Cx according the chip properties-related faults takes a maximum value 1 when period Px matches the chip period, and takes a value of 0 when the exposure period and the period Px is 0. There between it is linearly interpolated.

(II) The threshold value is set so as to detect whether there are chip properties-related faults. When the first local minimal point (negative value) of the auto correlation function is larger than the threshold value, it is determined that there is no chip periodicity and Cx=0 is given. The same applies to the slit direction (y direction). In this manner, the first characteristic factors (Cx, Cy) relating to chip properties-related faults are defined.

Figure 38:
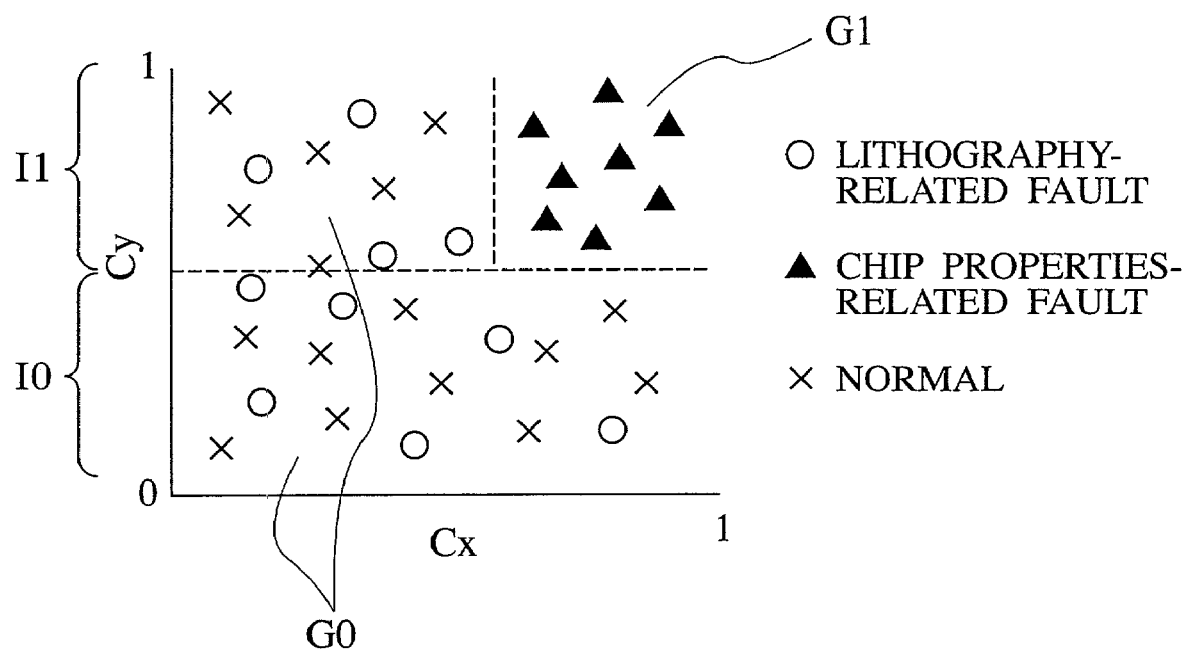
FIG. 38 is a graph that describes a method of detecting chip properties-related faults according to the first characteristic factors.

As shown in FIG. 38, the first characteristic factors (Cx, Cy) for a wafer having a lithography-related fault pattern and for a wafer having chip properties-related faults are found, respectively. Chip properties-related faults develop in the case where Cx and Cy are both equal to or greater than a certain threshold value. Accordingly, whether there are chip properties-based faults can be determined by whether (Cx, Cy) falls inside the region G1 in FIG. 38.

Figure 39:
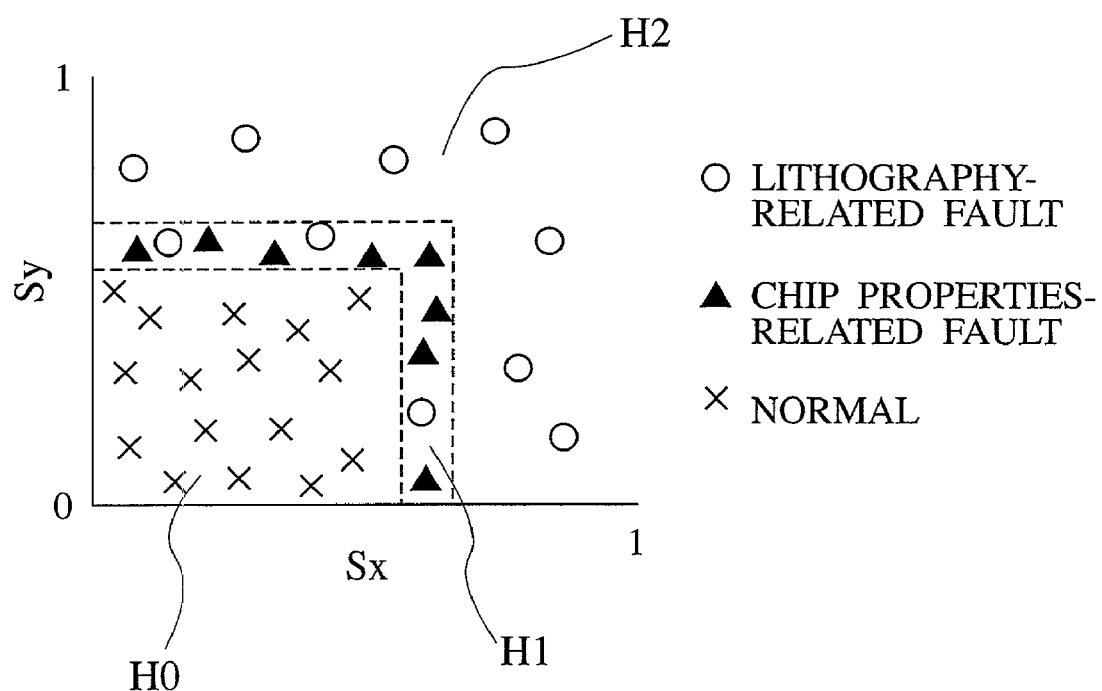
FIG. 39 is a graph that shows the distribution of characteristic factors of lithography-related faults and chip properties-related faults.

As shown in FIG. 39, the first characteristic factors (Sx, Sy) for a wafer having a lithography-related fault pattern and for a wafer having chip properties-related faults are found, respectively. Chip properties-related faults are distributed in a region H1 directly above a certain threshold value for lithography-related faults. Inversely, if they are lithography-related faults, the first characteristic factors of chip properties-related faults would not exceed the threshold value.

Accordingly, discrimination between lithography-related faults and chip properties-related faults can be performed in the following manner.

Lithography-related Fault Condition: (Sx, Sy) falls in the region H1 or the region H2, and when (Sx, Sy) falls in H1, (Cx, Cy) does not fall in the region G1.

Chip Properties-Related Fault Condition: (Cx, Cy) falls in the region G1.

Figure 40:
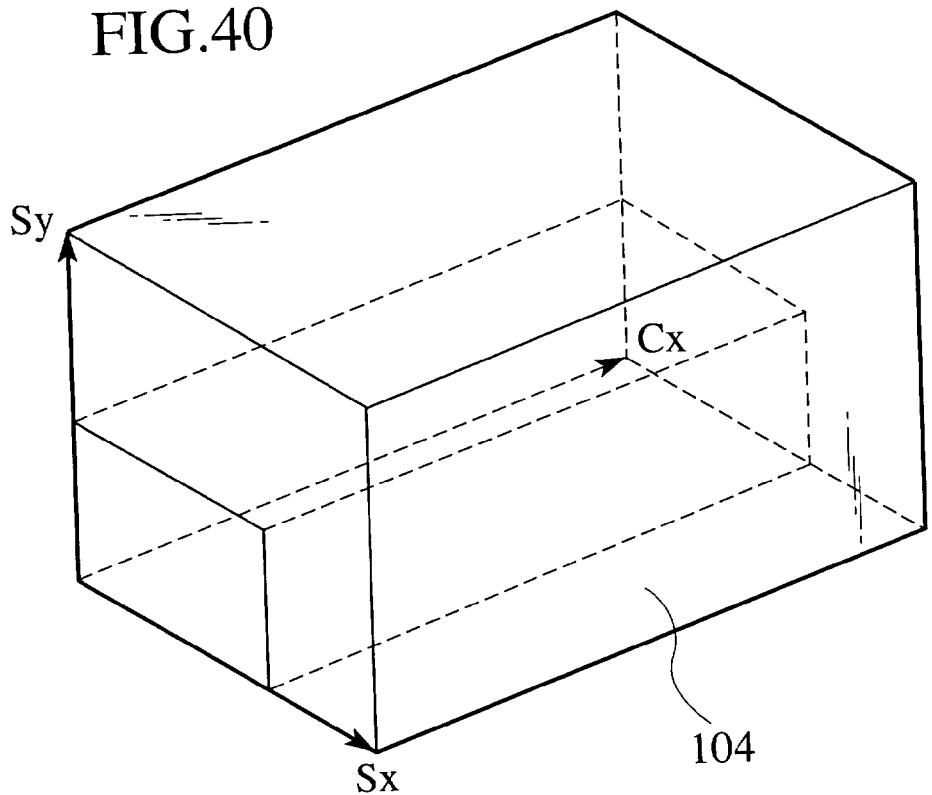
FIG. 40 is a perspective view showing the characteristic factors space and the lithography-related fault region in the case where there are no chip properties-related faults.

The discrimination is considered in the characteristic factors space having the vector (Sx, Sy, Cx, Cy). To begin with, as shown in FIG. 38, the region I0 at or below the threshold value for Cy and the region I1 at or above the threshold value are divided. FIG. 40 shows the case where Cy is in the region I0. In this case, the region H1 or H2 shows exposure-related faults 104 independent of the value of Cx.

Figure 41:
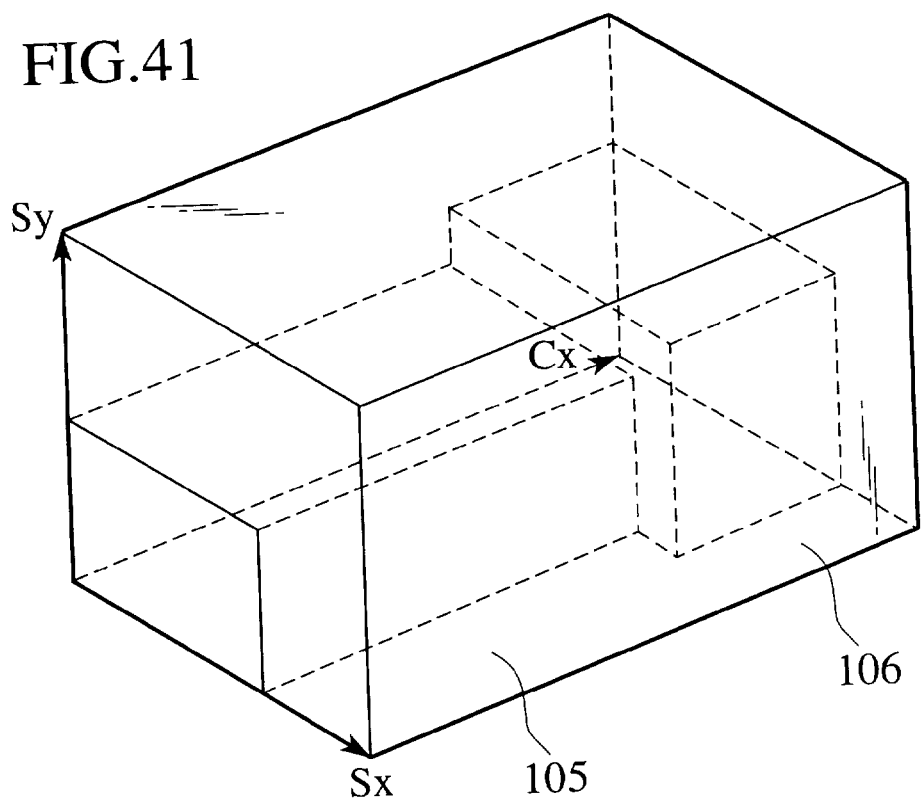
FIG. 41 is a perspective view showing the characteristic factors space and the lithography-related fault region in the case where chip properties-related faults partially exist.

On the other hand, FIG. 41 shows the case where Cy is in the region I0. In this case, if Cx is equal to or less than the threshold value, the region H1 or H2 shows exposure-related faults 105. In this case, if Cx is equal to or less than the threshold value, only the region H2 shows exposure-related faults 106. Fault mode determination can be performed using the characteristic factors space having first characteristic factors (Sx, Sy, Cx, Cy) in this manner. Confusion of the lithography-related faults and chip properties-related faults dependent on each other can be avoided.

As described above, according to the modification 1 of the sixth embodiment, discrimination of fault modes not independent of each other can be clearly identified and misdeterminations can be avoided.

(Modification 2 of the Sixth Embodiment)

With the sixth embodiment, a fault region within an n-D characteristic factors space configured by n-number of characteristic factors can be set. The fault mode is specified depending on whether a vector with the first characteristic factors comes into the fault region. With the modification 1 of the sixth embodiment, the mode specifying accuracy can be improved by setting complicated fault regions. Here it is determined whether there is a fault mode or not.

However, in the case where a vector having the first characteristic factors is near the threshold value of a fault region, and in the case where positioned in the center of the fault region, the "degree" of the fault mode differs. More specifically, if near the threshold value, the degree is lighter. Moreover, there are cases where statistical testing is performed for the development circumstances of the respective fault modes. In this case, it would be convenient if the fault mode existence were represented as a single numeric value (scalar amount). Accordingly, it is desirable that the fault mode be represented as a scalar amount further including that degree.

Figure 42:
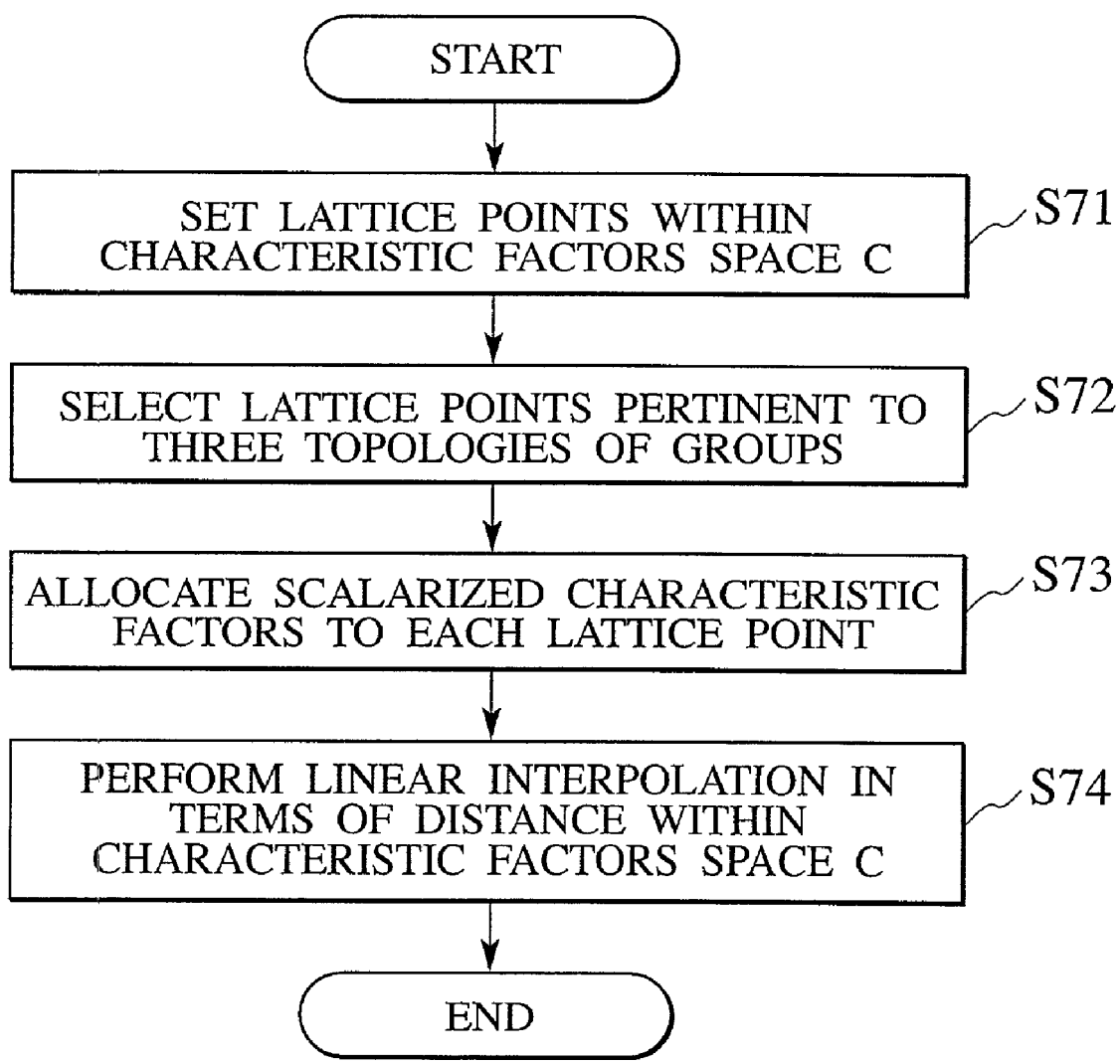
FIG. 42 is a flowchart showing a method of calculating scalarized characteristic factors according to the modification 2 of the sixth embodiment.

Therefore, the modification 2 of the sixth embodiment is described regarding a method that applies third characteristic factors having scalar amounts for the respective fault modes defined in the characteristic factors space while referencing FIG. 42. More specifically, a characteristic factors space C represented with first characteristic factors (C1, C2, ..., Cn) is considered. It is given that there is a defined fault mode A in a fault region within characteristic factors space C. A method for calculating the third characteristic factors (scalarized characteristic factors f) for a fault mode A is described forthwith.

(I) In stage S71, lattice points within characteristic factors space C are set. In stage S72, the lattice points pertaining to the three topologies of groups shown below are selected. More specifically, the three following topologies of groups are set.

Group L: a group of lattice points showing the situation where fault mode does not exist at all Group T: a group of lattice points positioned above a threshold value for fault mode A Group U: a group of lattice points showing the situation where fault mode has the strongest existence (II) In stage S73, the scalarized characteristic factors f that have been standardized are assigned to selected lattice points. More specifically, f=0 is assigned to the lattice point pertaining to group L. The lattice point pertaining to group U is assigned f=1. The lattice point pertaining to group T is assigned f=0.5.

(III) In stage S74, linear interpolation is performed relating to distances within the characteristic factors space C are set. Namely, linear interpolation is performed on lattice point Pi, which pertains to none of group L, group T, or group U. The scalar characteristic factors f are assigned to these lattice points depending on the distance to the respective lattice points pertaining to the groups L, T, and U.

More specifically, determination of whether the lattice point Pi pertains to the fault region showing the fault mode A is performed. If the lattice point Pi should in fact pertain to the fault region, the scalarized characteristic factors f can be assigned to lattice point Pi using expression (17). If the lattice point Pi does not pertain to the fault region, the scalarized characteristic factors f can be assigned to lattice point Pi using expression (18).

$$f(Pi)=0.5\times(1+/[Tk\ Pi]/(/[Tk\ Pi]+/[Pi\ Uj])) \quad (17)$$

$$f(Pi)=0.5\times/[L1Pi]/(/[L1Pi]+/[Pi\ Tk]) \quad (18)$$

where L1, Tk, and Uj are lattice points pertaining to groups L, T, and U, which are respectively closest to lattice point Pi, and /[Tk Pi], /[Pi Uj], /[L1 Pi], and /[Pi Tk] represent the distance between Tk and Pi, between Pi and Uj, between L1 and Pi, and between Pi and Tk, respectively.

Figure 43:
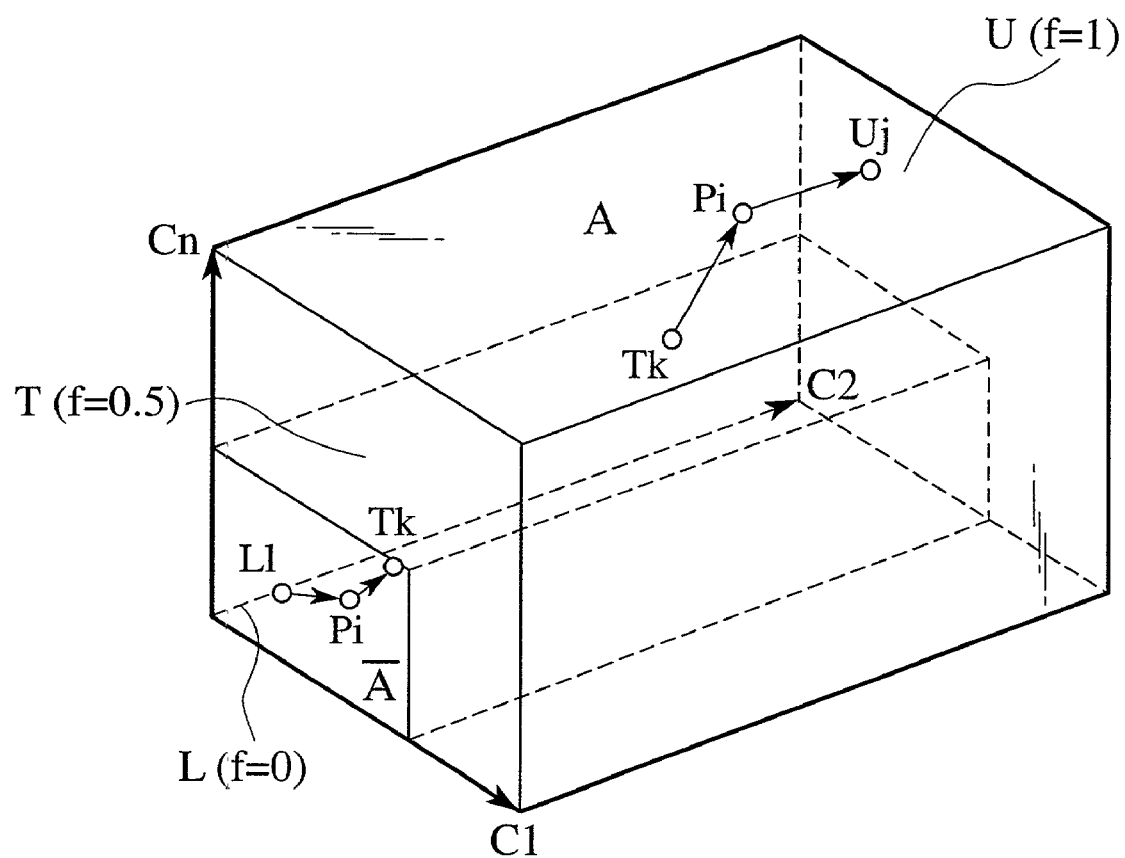
FIG. 43 is a perspective view that describes a method of determining scalarized characteristic factors for each lattice point.

As shown in FIG. 43, linear interpolation is performed in terms of the length of the bent line from L1 to Pi to Tk, or from Tk to Pi to Uj. It is noted that scalarized characteristic factors f can also be assigned to an arbitrary point P (C1, C2, ..., Cn), for which lattice points have not been set within characteristic factors space C. f(P), which is obtained by performing further linear interpolation of f(Pi) that was calculated in terms of each lattice point Pi, is assigned to arbitrary point P. For example, f can be approximated with the following P-th degree polynomial equation (equation (19)) relating to C1, C2, ..., Cn. The coefficients a1, a2, ..., am in equation (19) may be calculated using the method of least square shown in equation (20).

$$f(C1, C2, \Lambda, Cn) = a1C1^P + a2C1^{P-1}C2 + \Lambda + am \quad (19)$$

$$a1\sum_j (K1_j)^2 + a2\sum_j K1_jK2_j + \ldots + am\sum_j K1_jKm_j = \sum_j f_jK1_j$$

$$a2\sum_j K1_jK2_j + a2\sum_j (K2_j)^2 + \ldots + am\sum_j K2_jKm_j = \sum_j f_jK2_j$$

$$am\sum_j K1_jKm + a2\sum_j K2_jKm_j + \ldots + am\sum_j (Km_j)^2 = \sum_j f_jKm_j \quad (20)$$

where $K1=C1^P$, $K2=C1^{P-1}C2$ and Km=1. Instead of using equation (19) and equation (20), it is acceptable to perform linear interpolation using the value of adjacent lattice point Pi.

The case where this is applied to a lithography-related fault pattern is described by way of an example. The first characteristic factors (C1, C2) are found for the scanning exposure scan direction and slit direction, respectively. Respective threshold values are provided for the first characteristic factors. The lithography-related faults are classified with the threshold value as the basis.

Meanwhile, there are cases where statistical testing is carried out for all of the respective fault modes. In this case, it is more desirable for the existence of lithography-related faults to be represented by a scalar amount than represented by a vector amount. The vector amount illustrates a vector having the first characteristic factors (C1, C2). The scalar amount illustrates the third characteristic factor f (scalarized characteristic factor). For example, in the case where statistical testing is performed for yield (=scalar amount), it is desirable the yield be replaced with the scalarized characteristic factor f.

Figure 44:
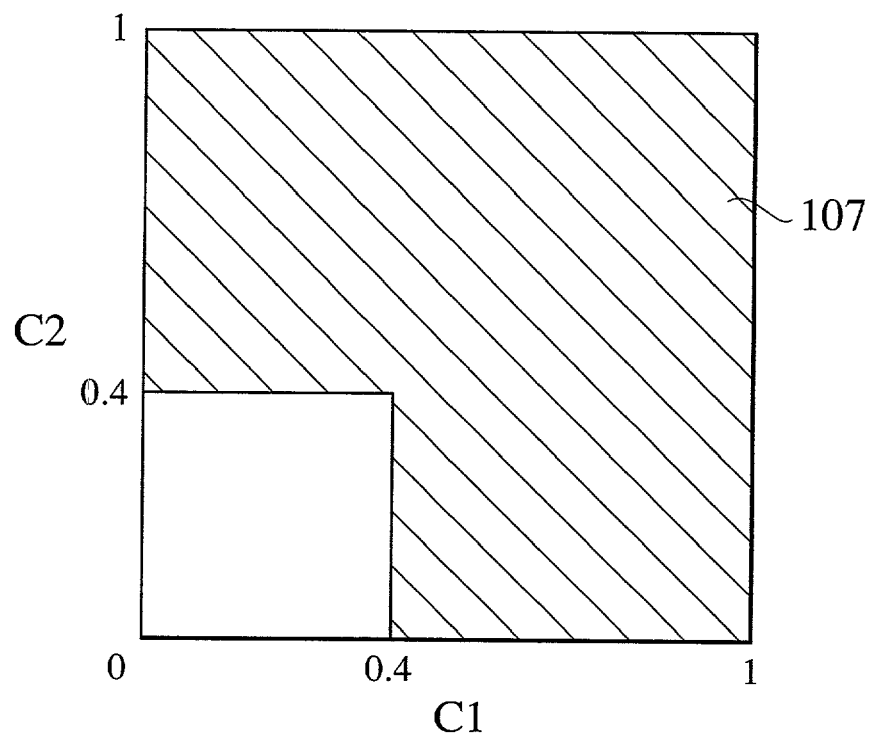
FIG. 44 is a planar view representing an entirety of shot properties-related faults in the characteristic factors space having the exposure-related first characteristic factors.
Figure 45:
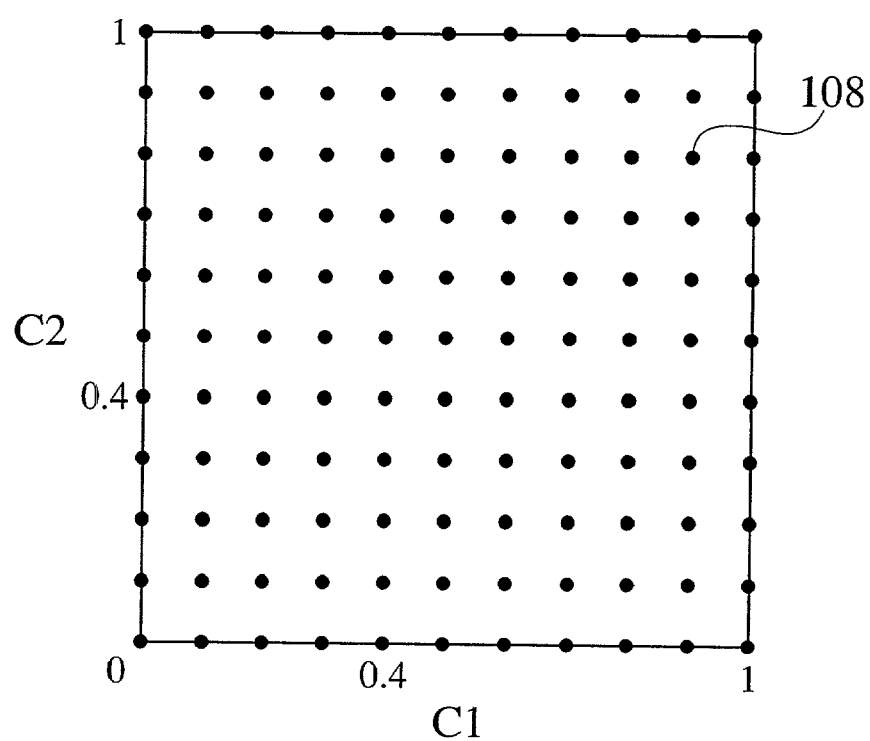
FIG. 45 is a planar view showing the lattice points set within the characteristic factors space of FIG. 44.

FIG. 44 shows the characteristic factors space having the first characteristic factors (C1, C2). The threshold value of both C1 and C2 is 0.4. When at least one of C1 and C2 exceeds 0.4, it is determined that there is a lithography-related fault. Accordingly, the slanted line portion 107 of FIG. 44 shows the overall lithography-related faults. As shown in FIG. 45, lattice points 108 are set at intervals of 0.1 for the characteristic factors space of FIG. 44.

Figure 46:
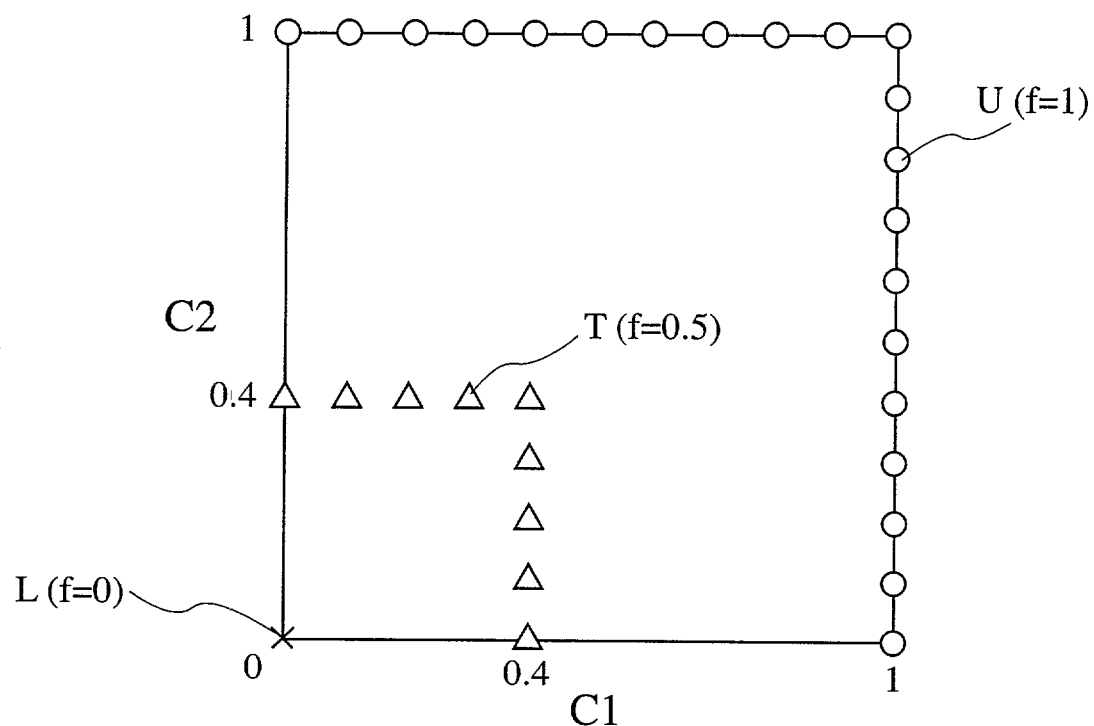
FIG. 46 is a planar view showing the lattice points pertaining to groups L, U and T.

Next, as shown in FIG. 46, lattice points pertaining to groups L, T, and U are determined. Group L shows a condition of zero for both C1 and C2. Group U shows a condition where the strongest existence of lithography-related faults. Here, group U shows a condition where there is separate and the strongest polarization existing in the scan direction (C1=1, and C2 is arbitrary), and a condition where there is separate and the strongest polarization existing in the slit direction (C2=1, and C1 is arbitrary). The lattice points positioned upon the boundary between lithography-related faults existing or not pertains to group T. Scalarized characteristic factor f=0 is assigned to the lattice point pertaining to group L. Scalarized characteristic factor f=1 is assigned to the lattice point pertaining to group U. Scalarized characteristic factor f=0.5 is assigned to the lattice point pertaining to group T.

Figure 47:
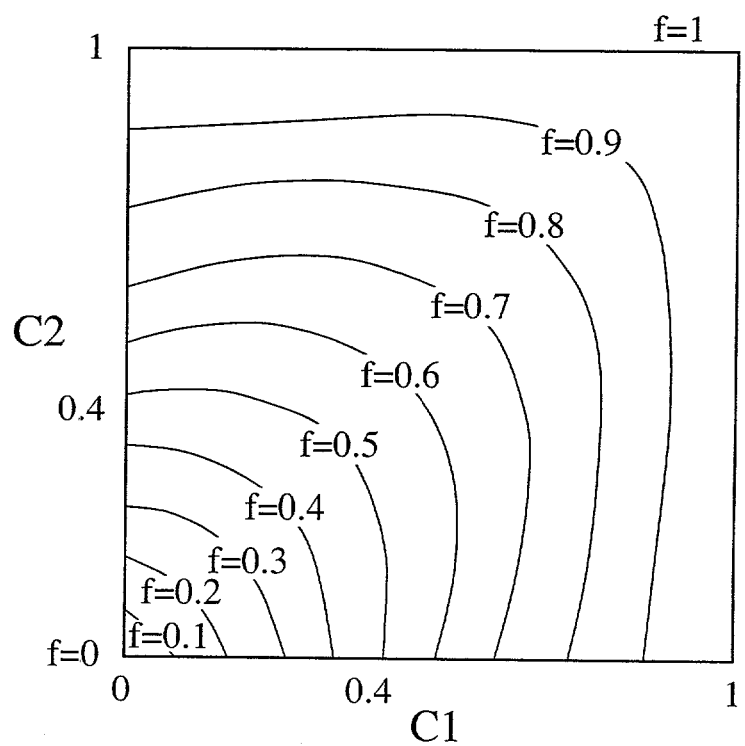
FIG. 47 is a contour map of the scalarized characteristic factors representing all of the lithography-related faults.

As shown in FIG. 47, the scalarized characteristic factor f (C1, C2) within the characteristic factors space is defined using the equations (17) through (20). The scalarized characteristic factor f is allocated to an arbitrary lattice point Pi in the characteristic factors space, and an arbitrary point P, which is not a lattice point. Upon the region L, f=0, upon the region U, f=1, and near the region T, f=0.5, and there between linear interpolation is successively performed. It is noted that FIG. 47 is represented by a 4-degree polynomial relating to C1 and C2. All of the lithography-related faults represented by the 2-D vector (C1, C2) along with the degree thereof are quantified with a scalar amount referred to as f(C1, C2).

Figure 35:
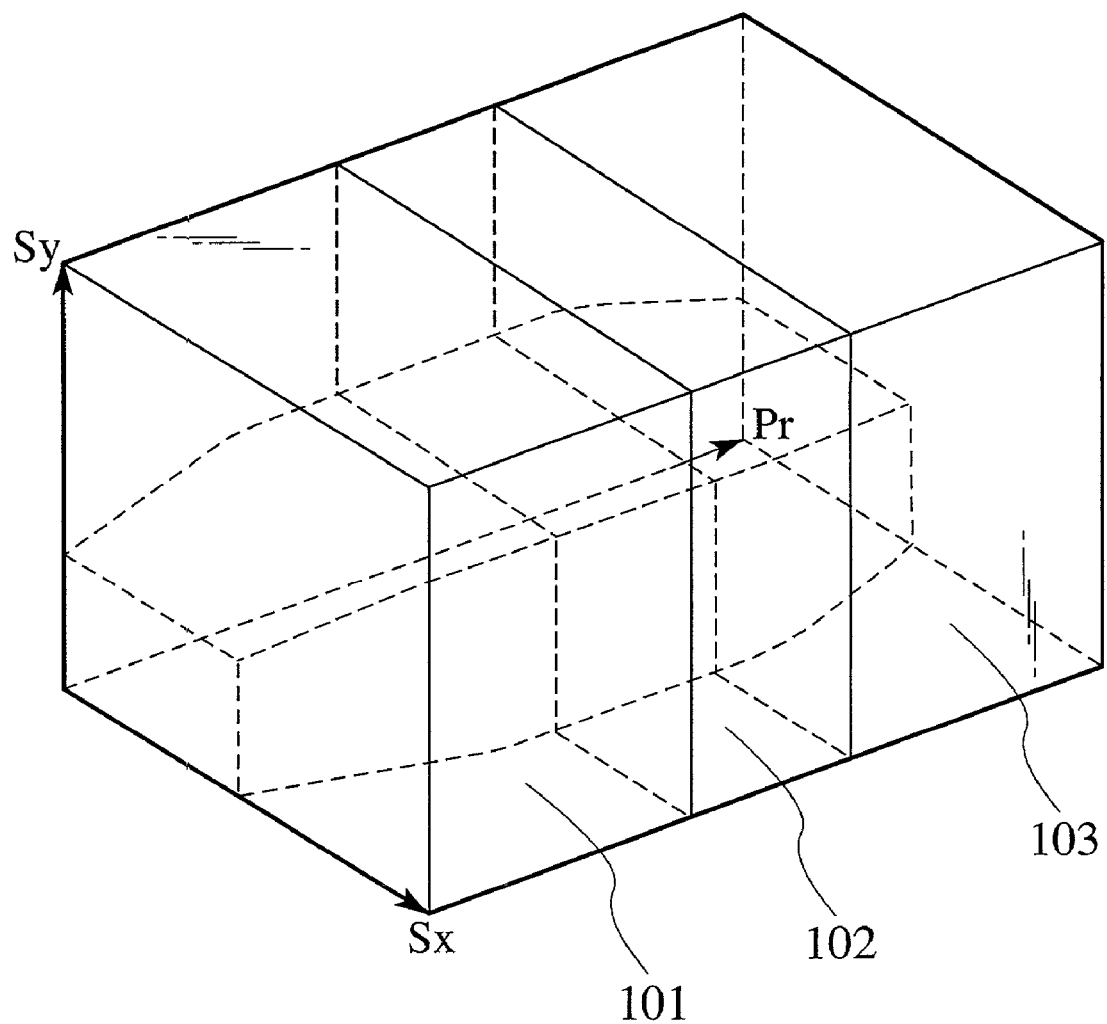
FIG. 35 is a perspective view showing the characteristic factors space after correction of the threshold value for the lithography-related faults.

The modification 2 of the sixth embodiment is particularly effective when region setting is made complicated. As shown in FIG. 35, even if the threshold values are corrected in response to the intra-surface distribution Pr, it is possible to mechanically establish scalarized characteristic factors f(Sx, Sy, Pr). The groups L, U, and T are set as shown in the following:

Group L: lattice points upon a straight line where (Sx, Sy, Pr)=(0, 0, t), and 0<=t<=1

Group U: lattice points upon a plane where Sx=1 and Sy=1

Group T: lattice points upon a curved surface formed by a corrected threshold value As shown in FIG. 40 and 41, the same is true for the case where a fault region within a 4-D space (Sx, Sy, Cx, Cy) is set.

By combining a plurality of characteristic factors spaces, it is possible to perform even more complicated mode classification. For example, a 5-D characteristic factors space represented by (Sx, Sy, Cx, Cy, Pr) can be considered through the combination of the characteristic factors spaces shown in FIG. 35, FIG. 40, and FIG. 41. The fault region in this characteristic factors space is set considering the following items:

1. Lithography-related faults
2. Intra-surface distribution of lithography-related faults
3. Correction of determination threshold value for lithography-related faults based on intra-surface distribution
4. Chip properties-related faults
5. Correction of determination threshold value for chip properties-related faults based on intra-surface distribution.

Figure 48:
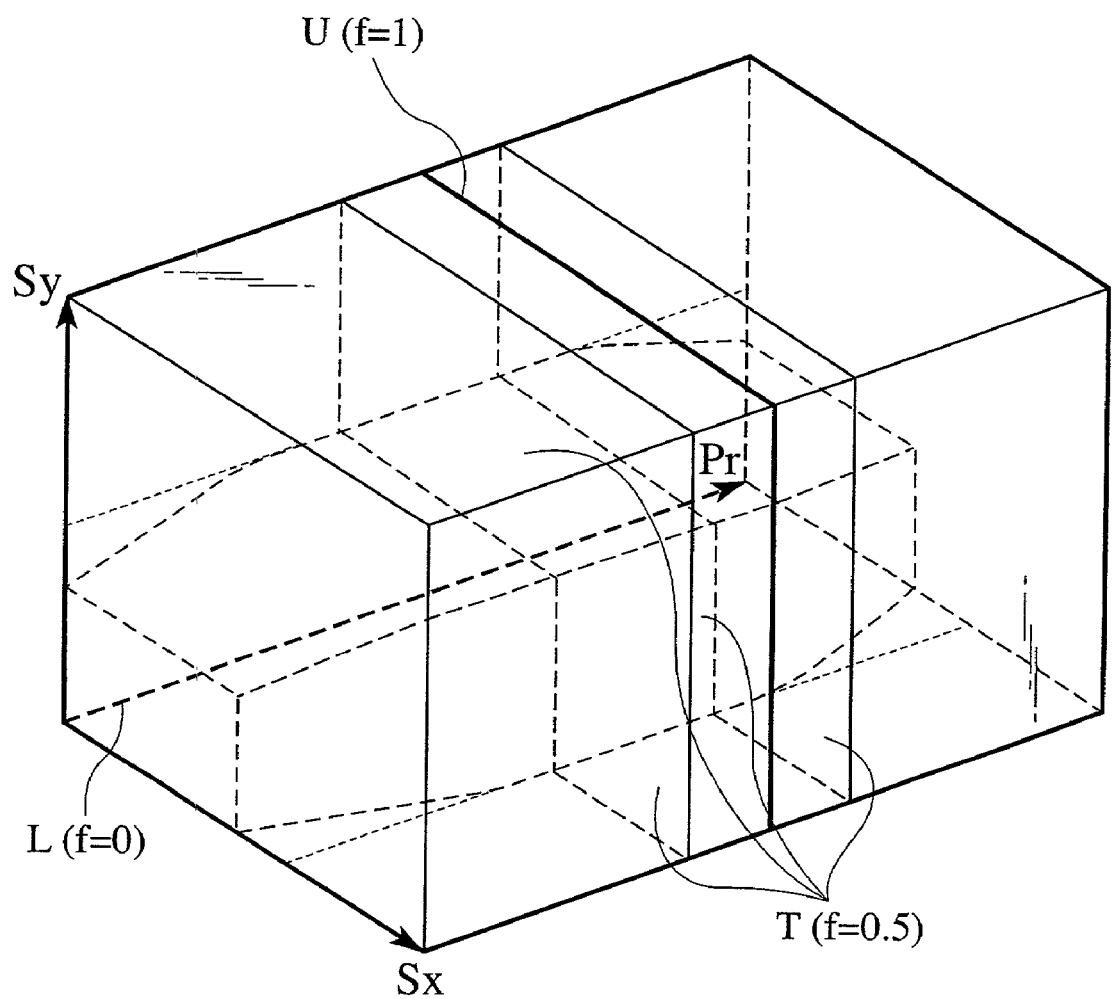
FIG. 48 is a perspective view showing a method of setting lattice points so as to calculate scalarized characteristic factors representing intra-surface uniform lithography-related faults.

It is noted that correction of the threshold value based on intra-surface distribution Pr is an operation that reduces the threshold value by a certain fixed percentage. Reduction is made with the same percentage for the threshold value correction in response to (Cx, Cy). Utilizing this region setting, it is possible to classify, for example, the following fault modes:

1. Overall lithography-related faults
2. Intra- surface uniform lithography-related faults
3. Intra-surface non uniform lithography-related faults
4. Wafer center polarized lithography-related faults
5. Wafer outer-circumference polarized lithography-related faults
6. Scan direction polarized lithography-related faults
7. Slit direction polarized lithography-related faults
8. Chip properties-related faults Besides this, finer mode classification (for example, wafer center polarized/scan direction polarized lithography-related faults) can also be considered. If the groups U, T, and L are set for each fault mode, the scalarized characteristic factors f can be mechanically defined. For example, the case of intra-surface uniform lithography-related faults is shown in FIG. 48. It is noted that FIG. 48 shows in terms of the three axes (Sx, Sy, Pr) in the case where Cx and Cy are equal to or lower than the threshold value. Generally, the groups U and L can be easily determined from the range that the characteristic factors describing the fault modes thereof can take. The group U may favorably take lattice points upon a surface where Sx=1 and Sy=1, and upon a straight line where Pr=0.5. The group L may favorably take lattice points upon a straight line where (Sx, Sy)=0. The group T may be favorably allocated at lattice points at positions where determination has changed, which are located by referencing the mode determination results of the peripheral lattice points.

In this manner it is possible to mechanically define the scalarized characteristic factors f for each fault mode. It is easy to incorporate the scalarized characteristic factors f in a statistical processing system, which handles scalar amounts shown in the fourth and fifth embodiments. As a result, yield improvement results and a fault causing equipment for each fault mode may be specified. By introducing a characteristic factors space, fault patterns can be resolved into a vector space, making it possible to easily quantify and perform statistical processing.

The modified example 2 of the sixth embodiment freshly defines the scalarized characteristic factors f within the characteristic factors space. The scalarized characteristic factors f makes it possible to mechanically quantify for complicated mode classifications.

In addition, fault regions are set in a characteristic factors space formed by a plurality of first characteristic factors, and these fault regions fault modes are determined. Fine classification of fault modes can be performed with high precision. In addition, the scalarized characteristic factors f can be mechanically defined for fault modes where complicated condition are set. It is possible to easily quantify and perform statistical processing.

The present invention may be embodied in other specific forms without departing from the spirit or essential characteristics thereof. The embodiments are therefore to be considered in all respects as illustrative and not restrictive, the scope of the present invention being indicated by the appended claims rather than by the foregoing description, and all changes which come within the meaning and range of equivalency of the claims are therefore intended to be embraced therein.

What is claimed is:

1. An equipment for detecting faults in semiconductor integrated circuits comprising:
   a fault input unit to input fault information for a plurality of divisional units on a surface of said semiconductor integrated circuits formed on a semiconductor wafer;
   a superimposing unit providing superimposed fault information, including said fault information from said plurality of divisional units;
   a first characteristic factor calculation unit to calculate a first characteristic factor showing a degree to which a fault of one of said plurality of divisional units is repeated within another of said plurality of divisional units from said superimposed fault information; and
   a clustering factor calculation unit to calculate a second characteristic factor representing a degree of polarization in a fault distribution within said semiconductor surface;
   wherein said first characteristic factor calculation unit determines whether said faults are detected with said second characteristic factor but not detected with said first characteristic factor.

2. The equipment of claim 1, further comprising an abnormal region removal unit to delete abnormal fault information from said fault information before providing superimposed fault information.

3. The equipment of claim 1, further comprising an abnormal region removal unit to determine abnormal fault information, when a total of said fault information of a first one of the plurality of divisional units is greater than the fault information of each of the plurality of divisional units surrounding the first one of the plurality of divisional units.

4. The equipment of claim 2, wherein said abnormal region removal unit determines said abnormal fault information, when a total of said fault information of a first one of the plurality of divisional units is greater than the fault information of each of the plurality of divisional units surrounding the first one of the plurality of divisional units.

5. The equipment of claim 1, wherein said first characteristic factor calculation unit determines from said superimposed fault information whether said fault is repeated by comparing said first characteristic factor with a predetermined threshold value.

6. The equipment of claim 1, wherein the first characteristic factor shows a degree to which a plurality of faults of one of said plurality of divisional units are repeated within another of said plurality of divisional units from said superimposed fault information.

* * * * *